US012290549B2

(12) United States Patent
Kishnani et al.

(10) Patent No.: US 12,290,549 B2
(45) Date of Patent: *May 6, 2025

(54) METHOD OF REDUCING TITERS OF ANTIBODIES SPECIFIC FOR A THERAPEUTIC AGENT

(71) Applicant: Duke University, Durham, NC (US)

(72) Inventors: Priya S. Kishnani, Durham, NC (US); Suhrad G. Banugaria, Durham, NC (US); Dwight D. Koeberl, Durham, NC (US); Sean N. Prater, Durham, NC (US)

(73) Assignee: Duke University, Durham, NC (US)

( * ) Notice: Subject to any disclaimer, the term of this patent is extended or adjusted under 35 U.S.C. 154(b) by 1149 days.

This patent is subject to a terminal disclaimer.

(21) Appl. No.: 17/125,885

(22) Filed: Dec. 17, 2020

(65) Prior Publication Data

US 2021/0177928 A1 Jun. 17, 2021

Related U.S. Application Data

(62) Division of application No. 15/796,137, filed on Oct. 27, 2017, now Pat. No. 10,869,906, which is a division of application No. 15/438,375, filed on Feb. 21, 2017, now Pat. No. 10,028,993, which is a division of application No. 14/454,137, filed on Aug. 7, 2014, now Pat. No. 9,592,247, which is a division of application No. 13/696,388, filed as application No. PCT/US2011/000800 on May 6, 2011, now Pat. No. 8,809,282.

(60) Provisional application No. 61/332,148, filed on May 6, 2010.

(51) Int. Cl.
| | |
|---|---|
| *A61K 38/05* | (2006.01) |
| *A61K 31/00* | (2006.01) |
| *A61K 31/519* | (2006.01) |
| *A61K 31/69* | (2006.01) |
| *A61K 38/17* | (2006.01) |
| *A61K 39/395* | (2006.01) |
| *C07K 16/28* | (2006.01) |
| *A61K 39/00* | (2006.01) |

(52) U.S. Cl.
CPC .............. *A61K 38/05* (2013.01); *A61K 31/00* (2013.01); *A61K 31/519* (2013.01); *A61K 31/69* (2013.01); *A61K 38/1722* (2013.01); *A61K 39/3955* (2013.01); *C07K 16/2887* (2013.01); *A61K 2039/505* (2013.01); *A61K 2039/545* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 4,510,130 A | 4/1985 | Platt et al. | |
| 7,056,712 B2 | 6/2006 | Chen | |
| 7,531,526 B2 | 5/2009 | Adams et al. | |
| 2004/0167139 A1 | 8/2004 | Potter | |
| 2005/0002945 A1 | 1/2005 | McBride et al. | |
| 2009/0110688 A1 | 4/2009 | Fertig et al. | |
| 2013/0052189 A1 | 2/2013 | Kishnani et al. | |
| 2014/0135337 A1* | 5/2014 | Joseph | A61P 7/06 514/249 |

OTHER PUBLICATIONS

Dilrukshi Senarathne et al., Non-specificity of symptoms in infantile-onset Pompe disease may delay the diagnosis and institution (BMJ Case Rep 2022; pp. 1-8.*
Linthorst., et al., 2004, Kidney International, vol. 66, pp. 1589-1595.
Manno., et al., "Successful Transduction of Liver in Hemophilia by AAV-Factor IX and Limitations Imposed by the Host Immune Response." Nature Med, Mar. 2006, vol. 12, No. 3, pp. 342-347, (Epub Feb. 12, 2006).
Mendelsohn J., et al., "Elimination of Antibodies to Recombinant Enzyme in Pompe's Disease", N Engl J Med. Jan. 8, 2009, vol. 360 (2), pp. 194-195.
Miller., et al., "Abrogation of the Hematological and Biological Activities of the Interleukin-3/Granulocyte-Macrophage Colony-Stimulating Factor Fusion Protein PIXY321 by Neutralizing Anti-PIXY321 Antibodies in Cancer Patients receiving High-Dose Carboplatin." Blood, May 1999, vol. 93, No. 10, pp. 3250-3258.
Moreau P., et al., "Prospective Comparison of Subcutaneous Versus Intravenous Administration of Bortezomib in Patients with Multiple Myeloma", Haematologica 93(12), Dec. 2008, Epub. Sep. 2, 2008, pp. 1908-1911.
Muenzer J., "The Mucopolysaccharidoses: A Heterogeneous Group of Disorders with Variable Pediatric Presentations", Journal of Pediatrics, May 2004, vol. 144, pp. S27-S34, (5 Suppl).
"Myozyme Alglucosidase Alfa; data sheet" downloaded Jan. 7, 2020, pp. 1-11.
Nandedkar., "Nanovaccines: recent developments in vaccination." J Biosci, Dec. 2009, vol. 34, No. 6, pp. 995-1003.
Neubert., et al., "The Proteasome Inhibitor Bortezomib Depletes Plasma Cells and Protects Mice with Lupus-like Disease from Nephritis." Nat Med, Jul. 2008, vol. 14, No. 7, pp. 748-755 (Epub Jun. 8, 2008).

(Continued)

*Primary Examiner* — Robert M Kelly
(74) *Attorney, Agent, or Firm* — Polsinelli PC

(57) ABSTRACT

The present invention relates, in general, to a method of treating patients undergoing enzyme replacement therapy (ERT) or other therapy involving the administration of a proteinaceous therapeutic agent as well gene replacement therapy with non-viral or viral vectors, or other therapeutic modality or modalities, used alone or in combination, which involve the administration of exogenous substances for potential therapeutic benefit, including, but not limited to DNA vaccines, siRNA, splice-site switching oligomers (SSOs) as well as RNA-based nanoparticles (RNPs) and nanovaccines. The invention further relates to compounds and compositions suitable for use in such methods.

16 Claims, 10 Drawing Sheets

(56) References Cited

OTHER PUBLICATIONS

Nicolino., et al., "Clinical Outcomes after Long-Term Treatment with Alglucosidase Alfa in Infants and Children with Advanced Pompe Disease." Genet Med, Mar. 2009, Issue. 11, vol. 3, pp. 210-219.
Ozpolat., et al., "Nanomedicine Based Approaches for the Delivery of SiRNA in Cancer." J Intern Med, Jan. 2010, Issue. 267, vol. 1, pp. 44-53.
Parkinson L E., et al., "Lysosomal Storage Disease Revealing Lysosomal Function and Physiology", Physiology, Apr. 2010, vol. 25, pp. 102-115.
Phupong V., et al., "Prenatal Diagnosis of Pompe Disease by Electron Microscopy", Arch Gynecol Obstet, 271(3), Mar. 2005, Epub. May 14, 2004, pp. 259-261.
Piva R., et al., "CEP-18770: A novel, Orally Active Proteasome Inhibitor with a Tumor-Selective Pharmacologic Profile Competitive with Bortezomib", Blood 111(5), Mar. 2008, Epub. Dec. 5, 2007, pp. 2765-2775.
Raben., et al., "Targeted Disruption of the Acid Alpha-Glucosidase Gene in Mice Causes an Illness with Critical Features of both Infantile and Adult human Glycogen Storage Disease type II." J. Biol. Chem, Jul. 1998, vol. 273, No. 30, pp. 19086-19092.
Raben N., et al., "Deconstructing Pompe Disease by Analyzing Single Muscle Fibers: to see a World in a Grain of Sand", Autophagy 3(6), Nov.-Dec. 2007, Epub. Jun. 15, 2007, pp. 546-552.
Ragni., et al., "Risk Factors for Inhibitor Formation in Haemophilia: A Prevalent Case-control Study", Haemophilia, Sep. 2009, vol. 15, No. 5, pp. 1074-1082, (Epub Jun. 26, 2009).
Rodriguez N.I., et al., "Advances in Hemophilia: Experimental Aspects and Therapy", Pediatr Clin North Am, Apr. 2008, vol. 55, No. 2, pp. 357-376.
Rougeot C., et al., "Comparative Study of Biosynthetic Human Growth Hormone Immunogenicity in Growth Hormone Deficient Children", Horm Res, Year 1991, vol. 35, No. 2, pp. 76-81.
Shehata N., et al., "The Use of Immunoglobulin Therapy for Patients with Primary Immune Deficiency: An Evidence-based Practice Guideline", Transfusion Medicine Reviews, Jan. 2010, vol. 24, No. 1, pp. 28-50, (Supply 1).
Shirley R.B., et al., "Combination of Proteasomal Inhibitors Lactacystin and MG132 Induced Synergistic Apoptosis in Prostate Cancer Cells", Neoplasia, Dec. 2005, vol. 7, No. 12, pp. 1104-1111.
Soucy T.A., et al., "An Inhibitor of NEDD8-activating Enzyme as a New Approach to Treat Cancer", Nature, Apr. 9, 2009, vol. 458, No. 7239, pp. 732-736.
Staubli U., et al., "Chronic Administration of a Thiol-proteinase Inhibitor Blocks Long-term Potentiation of Synaptic Responses", Brain Research, Mar. 1988, vol. 444, pp. 153-158.
Sun B., et al., "Enhanced Response to Enzyme Replacement Therapy in Pompe Disease after the Induction of Immune Tolerance", American Journal of Human Genetics, Nov. 2007, vol. 81, No. 5, pp. 1042-1049, (Epub Sep. 21, 2007).
Sun B., et al., "Immunomodulatory Gene Therapy Prevents Antibody Formation and Lethal Hypersensitivity reactions in Murine Pompe Disease", Molecular Theraphy, Feb. 2010, vol. 18, No. 2, pp. 353-360, (Epub Aug. 18, 2009).
The Lenercept Multiple Sclerosis Study Group and The University of British Columbia MS/MRI Analysis Group, "TNF Neutralization in MS: results of a Randomized, Placebo-controlled Multicenter Study", Neurology, Aug. 1999, vol. 53, No. 3, pp. 457-465.
Tisdale M.J., "Is there a Common Mechanism Linking Muscle Wasting in Various Disease Types?", Current Opinion in Support Palliative Care, Dec. 2007, vol. 1, No. 4, pp. 287-292.
"Velcade® [Package Insert] Highlights of Prescribing Information", Cambridge (Mass.) Millennium Pharmaceuticals, Revised Dec. 2010, Inc. pp. 1-34.
Vogel M., et al., "Left Ventricular Myocardial Mass determined by Cross-sectional Echocardiography in Normal Newborns, Infants, and Children", Pediatr. Cardiol, Jul. 1991, vol. 12, No. 3, pp. 143-149.

Vogelbacher R., et al., "Bortezomib and Sirolimus Inhibit the Chronic Active Antibody-Mediated Rejection in Experimental Renal Transplantation in the Rat", Nephrology Dialysis Transplantation, vol. 25, Apr. 28, 2010, pp. 3764-3773.
Wadhwa M., et al., "Production of Neutralizing Granulocyte-macrophage Colony-stimulating factor (GM-CSF) Antibodies in Carcinoma Patients following GM-CSF Combination therapy", Clin. Exp. Immunol, May 1996, vol. 104, No. 2, pp. 351-358.
Wang J., et al., "Neutralizing Antibodies to Therapeutic Enzymes: Considerations for Testing, Prevention and Treatment", Nat Biotechnol, Aug. 2008, vol. 26, No. 8, pp. 901-908.
Williamson M.J., et al., "Comparison of Biochemical and Biological Effects of ML858 (salinosporamide A) and Bortezomib", Mol Cancer Ther, Dec. 2006, vol. 5, No. 12, pp. 3052-3061.
Written Opinion issued in International Application No. PCT/US2011/000800 filed on May 6, 2011 mailed on Jan. 19, 2012 (Applicant—Duke University // Inventors—Kishnani et al.) (5 pages).
Zhou H.J., et al., "Design and Synthesis of an Orally Bioavailable and Selective Peptide Epoxyketone Proteasome Inhibitor(PR-047)", J Med Chem, May 2009, vol. 52, No. 9, pp. 3028-3038.
Badalamente M A., et al., "Neuromuscular Recovery Using Calcium Protease Inhibition After Median Nerve Repair in Primates", Proc. Natl. Acad. Sci. U.S.A. 86(15), Aug. 1989, pp. 5983-5987.
Banugaria S G., et al., "Persistence of High Sustained Antibodies to Enzyme Replacement Therapy Despite Extensive Immunomodulatory Therapy in an Infant with Pompe Disease: Need for Agents to Target Antibody-Secreting Plasma Cells", Mol Genet Metab, Apr. 2012, vol. 105, Issue. 4, pp. 677-680.
Banugaria S.G., et al., "The Impact of Antibodies on Clinical Outcomes in Diseases Treated with Therapeutic Protein: Lessons learned from Infantile Pompe Disease", Genet Med, Aug. 2011, vol. 13, No. 8, pp. 729-736.
Beehler B.C., et al., "Reduction of Skeletal Muscle Atrophy by a Proteasome Inhibitor in a Rat Model of Denervation", Exp. Biol. Med. (Maywood), Mar. 2006, vol. 231, No. 3, pp. 335-341.
Bessis N., et al., "Immune Responses to Gene Therapy Vectors: Influence on Vector Function and Effector Mechanisms", Gene Theraphy, Oct. 2004, vol. 11, pp. S10-S (Suppl 1).
Bonetti P., et al., "Interferon Antibodies in Patients with Chronic Hepatitis C Virus Infection treated with Recombinant Interferon alpha-2 alpha", J Hepatol, Mar. 1994, vol. 20, No. 3, pp. 416-420.
Boutin S., et al., "Prevalence of Serum IgG and Neutralizing Factors Against Adeno-Associated Virus types 1, 2, 5, 6, 8 and 9 in the Healthy Population: Implications for Gene Therapy using AAV Vectors", Hum Gene Ther. 21(6), Jun. 2010, pp. 704-712.
Bray G.L., et al., "A Multicenter Study of Recombinant Factor VIII (recombinate): Safety, Efficacy, and Inhibitor Risk in previously untreated patients with Hemophilia A. The Recombinate Study Group", Blood, May 1994, vol. 83, No. 9, pp. 2426-2435.
Brooks D.A., "Immune Response to Enzyme Replacement Therapy in Lysosomal Storage Disorder Patients and Animal Models", Mol. Genet. Metab, Oct. 1999, vol. 68, No. 2, pp. 268-275.
Chatenoud L., et al., "Restriction of the Human in Vivo Immune Response Against the Mouse Monoclonal Antibody OKT3", J Immunol, 137(3), Aug. 1986, pp. 830-838.
Chauhan D., et al., "A Novel Orally Active Proteasome Inhibitor Induces Apoptosis in Multiple Myeloma Cells with Mechanisms Distinct from Bortezomib", Cancer Cell 8(5), Nov. 2005, pp. 407-419.
Delong R.K., et al., "Characterization and Performance of Nucleic Acid Nanoparticles Combined with Protamine and Gold", Biomaterials, Nov. 2009, vol. 30, No. 32, pp. 6451-6459.
Demo S.D., et al., "Antitumor Activity of PR-171, a Novel Irreversible Inhibitor of the Proteasome", Cancer Res, Jul. 2004, vol. 67, No. 13, pp. 6383-6391.
Dick L R., et al., "Building on Bortezomib: Second Generation Proteasome Inhibitors as Anti-Cancer Therapy", Drug Discovery Today, Mar. 2010, vol. 15, Issue. 5-6, pp. 243-249.
Dickson P., et al., "Immune Tolerance Improves the Efficacy of Enzyme Replacement Therapy in Canine Mucopolysaccharidosis I", J Clin Invest, 118(8), Aug. 2008, pp. 2868-2876.

(56) References Cited

OTHER PUBLICATIONS

"Donor-Specific Antibody From Wikipedia", The Free Encyclopedia, downloaded Jan. 7, 2020, pp. 1-3.
Dorsey B D., et al., "Discovery of a Potent, Selective, and Orally Active Proteasome Inhibitor for the Treatment of Cancer", J Med Chem. 51(4), Feb. 5, 2008, pp. 1068-1072.
"Endocrinologic and Metabolic Drugs Advisory Committee Meeting", 2003, pp. 1-129.
Everly M J., et al., "Bortezomib Provides Effective Therapy for Antibody and Cell-Mediated Acute Rejection", Transplantation 86(12), Dec. 2008, pp. 1754-1761.
Everly M J., et al., "Proteasome Inhibition Reduces Donor-Specific Antibody Levels", Transplantation Proc. 41:105-107, 2009, pp. 105-107.
Fineberg S E., et al., "Immunogenicity of Recombinant DNA Human Insulin", Diabetologia 25(6), Dec. 1983, pp. 465-469.
"Food and Drug Administration, Center for Biologics Evaluation and Reasearch", Meeting of the Biological Response Modifiers Advisory Committee, Jul. 1999, pp. 1-272.
Franco L M., et al., "Evasion of Immune Responses to Introduced Human Acid Alpha-Glucosidase by Liver-Restricted Expression in Glycogen Storage Disease Type II", Mol Ther. 12(5), Nov. 2005, Epub. Jul. 6, 2005, pp. 876-884.
Fuchs H J., et al., "Effect of Aerosolized Recombinant Human DNase on Exacerbations of Respiratory Symptoms and on Pulmonary Function in Patients with Cystic Fibrosis the Pulmozyme Study Group", N Engl J Med. 331(10), Sep. 1994, pp. 637-642.
Gazzerro E., et al., "Therapeutic Potential of Proteasome Inhibition in Duchenne and Becker Muscular Dystrophies", Am J Pathol, 176(4), Apr. 2010, Epub. Mar. 19, 2010, pp. 1863-1877.
Gneiss., et al., "Influence of Interferon-beta Therapy Switching on Neutralizing Antibody titres: results from the Austrian Switch Study." Mult. Scler, Dec. 2009, vol. 15, No. 12, pp. 1481-1488 (Epub Nov. 13, 2009).
Grabowski A G., et al "Enzyme Therapy Lysosomal Storage Disease: Principles Practice and Prospects", 2003, vol. 4, pp. 403-436.
Hall., "Immunomodulation with Intravenous Immunoglobulin." Pharmacotherapy, Nov. 1993, vol. 13, No. 6, pp. 564-573 (Dec. 1993).
Hartung., et al., "Significance of Neutralizing Antibodies to Interferon Beta during Treatment of Multiple Sclerosis: expert Opinions based on the Proceedings of an International Consensus Conference." Eur. J. Neurol. Aug. 2005, vol. 12, No. 8, pp. 588-601.
Hawes., et al., "Differential Muscular Glycogen Clearance after Enzyme Replacement therapy in a Mouse model of Pompe Disease." Mol Genet Metab, Aug. 2007, vol. 91, No. 4, pp. 343-351, (Epub Jun. 14, 2007).
Hirschhorn R., et al., "Glycogen Storage Disease Type II: Acid a-Glucosidase (Acid Maltase) Deficiency". Scriver's OMMBID the online metabolic & molecular bases of inherited disease. D. Valle and C. R. Scriver. New York, (2009), pp. 3389-3420, McGraw-Hill.
Hollak C E M., et al., "Immune Response to Enzyme Replacement Therapy in Fabry Disease: Impact on Clinical Outcome?" Mol Genet Metab , Jan. 2009, vol. 96, No. 1, pp. 1-3 (Epub Dec. 4, 2008).
Hout H.M., et al., "The Natural course of Infantile Pompe's Disease: 20 original cases compared with 133 cases from the literature", Pediatrics, Aug. 2003, vol. 112, No. 2, pp. 332-340.
Hug., "Pre- and Postnatal Pathology, Enzyme Treatment, and Unresolved Issues in Five lysosomal Disorders." Pharmacol Rev, (Dec. 1978), vol. 30, No. 4, pp. 565-591.
Hunley T E., et al., "Nephrotic Syndrome Complicating Alpha-Glucosidase Replacement Therapy for Pompe Disease", Pediatrics, Oct. 2004, 114(4):e532-e535, pp. 4.
International Preliminary Report issued in International Application No. PCT/US2011/000800 filed May 6, 2011 mailed on Nov. 15, 2012 (Duke University—Applicant // Kishnani et al.—Inventors) (7 pages).
International Search Report for International Application No. PCT/US2011/000800 filed May 6, 2011 dated Jan. 19, 2012 (Duke University—Applicant // Kishnani et al.—Inventors) (4 pages).
Jooss K., et al., "Immunity to Adenovirus and Adeno-Associated Viral Vectors: Implications for Gene Therapy", Gene Therapy, Jun. 2003, vol. 10, Issue. 11, pp. 955-963.
Kakkis., et al., "Successful Induction of Immune Tolerance to Enzyme Replacement Therapy in Canine Mucopolysaccharidosis I." Proc. Natl. Acad. Sci. USA Jan. 2004, vol. 101, No. 3, pp. 829-834 (Epub Jan. 8, 2004).
Kim K H., et al., "Successful Reduction of High-Sustained anti-Idursulfase Antibody Titers by Immune Modulation Therapy in a Patient with Severe Mucopolysaccharidosis Type II", Molecular Genetics and Metabolism Reports 2, 2015, pp. 20-24.
Kishnani., et al., "A Retrospective, Multinational, Multicenter Study on the Natural History of Infantile-Onset Pompe Disease." J Pediatr, (May 2006) , vol. 148, No. 5, pp. 671-676.
Kishnani., et al., "Cross-Reactive Immunologic Material Status Affects Treatment Outcomes in Pompe Disease Infants." Mol. Genet. Metab, Jan. 2010, vol. 99, No. 1, pp. 26-33.
Kishnani., et al., "Early Treatment with Alglucosidase Alpha Prolongs Long-term Survival of Infants with Pompe Disease." Pediatr Res, Sep. 2009, vol. 66, No. 3, pp. 329-335.
Kishnani., et al., "Recombinant Human Acid [alpha]-Glucosidase: Major Clinical Benefits in Infantile-Onset Pompe Disease." Neurology, Jan. 2007, vol. 68, No. 2, pp. 99-109, Epub Dec. 6, 2006.
Kishnani.,et al., "Chinese Hamster Ovary Cell-Derived Recombinant Human Acid Alpha-Glucosidase in Infantile-Onset Pompe Disease." J Pediatr, Jul. 2006, vol. 149, No. 1, pp. 89-97.
Kling., et al., "Safety and Efficacy of Recombinant Acid Alpha-Glucosidase (rhGAA) in Patients with Classical Infantile Pompe Disease: results of a Phase II Clinical Trial." Neuromuscul. Disord, Jan. 2005, vol. 15, No. 1, pp. 24-31. Epub Nov. 26, 2004.
Kupperman., et al., "Evaluation of the Proteasome Inhibitor MLN9708 in Preclinical Models of Human Cancer." Cancer Res, Mar. 2010, vol. 70, No. 5, pp. 1970-1980.(Epub Feb. 16, 2010).
Langford-Smith K J., et al., "Heparin Cofactor II-Thrombin Complex and Dermatan Sulphate:Chondroitin Sulphate Ratio are Biomarkers of Short- and Long-Term Treatment Effects in Mucopolysaccharide Diseases", J Inherit Metab Dis, Apr. 2011, vol. 34, Issue. 2, pp. 499-508.
Lecker., et al., "Muscle Protein Breakdown and the Critical Role of the Ubiquitin-Proteasome Pathway in Normal and Disease States." J. Nutr, Jan. 1999, vol. 129, (1S Suppl), pp. 227S-237S.
Levine M H., et al., "Treatment Options and Strategies for Antibody Mediated Rejection after Renal Transplantation", Seminars in Immunology, Apr. 2012, vol. 24, Issue. 2, pp. 136-142.

* cited by examiner

METHOD OF REDUCING TITERS OF ANTIBODIES SPECIFIC FOR A THERAPEUTIC AGENT

CROSS-REFERENCE TO RELATED APPLICATIONS

This application is a divisional of U.S. application Ser. No. 15/796,137 (now U.S. Pat. No. 10,869,906), filed Oct. 27, 2017, which is a divisional of U.S. application Ser. No. 15/438,375 (now U.S. Pat. No. 10,028,993), filed Feb. 21, 2017, which is a divisional of U.S. application Ser. No. 14/454,137 (now U.S. Pat. No. 9,592,247), filed Aug. 7, 2014, which is a divisional of U.S. application Ser. No. 13/696,388 (now U.S. Pat. No. 8,809,282), filed Nov. 6, 2012, which is a U.S. national phase of International Application No. PCT/US2011/000800, filed May 6, 2011, which designated the U.S. and claims benefit of U.S. Provisional Application No. 61/332,148, filed May 6, 2010, the entire contents of each of which are incorporated herein by reference.

TECHNICAL FIELD

The present invention relates, in general, to a method of reducing antibody titers or preventing the formation of antibody titers and, in particular, to a method of reducing/preventing antibody titers and/or for clinical benefit in patients undergoing protein replacement therapy (PRT) or other therapy involving the administration of a proteinaceous therapeutic agent. The invention also relates to gene replacement therapy with non-viral or viral vectors, or other therapeutic modality or modalities, used alone or in combination, which involve the administration of exogenous substances for potential therapeutic benefit, including, but not limited to, DNA vaccines, siRNA, splice-site switching oligomers (SSOs) as well as RNA-based nanoparticles (RNPs) and nanovaccines. The invention also relates to compounds and compositions suitable for use in such methods therapies.

BACKGROUND

Alpha-glucosidase (E.C 3.2.1.20) (also known as acid maltase glucoinvertase, glucosidosucrase, maltase-glucoamylase, α-glucopyranosidase, glucosidoinvertase, α-D-glucosidase, acid alpha glucosidase, α-glucoside hydrolase, and α-1,4-glucosidase) (GAA) is an enzyme involved in hydrolysis of terminal, non-reducing (1→4)-linked α-D-glucose residues with the release of α-D-glucose. A deficiency of this enzyme results in Pompe disease (also known as glycogen storage disease type II, GSD II/GSD 2, type 2 glycogenosis, acid maltase deficiency, alpha glucosidase deficiency, alpha-1,4-Glucosidase deficiency, cardiomegalia glycogenica diffusa, generalized glycogenosis, lysosomal alpha glucosidase deficiency or lysosomal glucosidase deficiency), which is an autosomal recessive lysosomal storage disorder. Pompe disease is characterized by pathological accumulation of glycogen in lysosomes of multiple tissues (Hirschhorn and Reuser, Glycogen Storage Disease Type II: Acid a-Glucosidase (Acid Maltase) Deficiency, Internet Computer File Date of Entry: 20090331, New York: McGraw-Hill (2009)—available from: URL:genetics-dot-accessmedicine-dot-com/). Myocytes within skeletal, cardiac and smooth muscles are disproportionately involved. Glycogen accumulation in these tissues can occur rapidly. Glycogen accumulation has been detected in fetuses as young as 16-18 weeks gestational age (Hug 1978; Phupong, Shuangshoti et al. 2005).

The classical, infantile form of Pompe disease is considered the most severe within the spectrum of Pompe phenotypes and is characterized by cardiomyopathy, hypotonia, and respiratory insufficiency. Many infantile Pompe disease patients are living longer and are experiencing enhanced quality of life as a result of rhGAA (alglucosidase alfa, Myozyme®, Lumizyme®, Genzyme Corporation, Massachusetts, USA) enzyme replacement therapy (ERT) (Kishnani et al, Neurology 68(2):99-109 (2007), Kishnani et al, Pediatr. Res. 66(3):329-335 (2009), (Kishnani, Corzo et al. 2007; Kishnani, Corzo et al. 2009; Nicolino, Byrne et al. 2009) (see also U.S. Pat. No. 7,056,712). Without effective ERT with rhGAA, death typically occurs secondary to cardiorespiratory failure within the first one to two years of life (van den Hout, Hop et al. 2003; Kishnani, Hwu et al. 2006; Hirschhorn and Reuser 2009). This is in contrast to the juvenile and adult-onset forms (late-onset Pompe disease), where skeletal and respiratory muscle weakness predominates. Overall, there is an inverse correlation between disease severity and the level of residual enzyme activity. The most severely affected individuals have little to no detectable GAA activity. Such patients typically present during infancy (Hirschhorn and Reuser 2009).

In addition to GAA activity, there are additional factors known to affect outcome in patients with Pompe disease. These include, but are not necessarily limited to, age upon ERT initiation, extent of preexisting pathology, the degree of muscle damage as well as the muscle fiber type (i.e., type I vs. type II) with greatest relative involvement as well as defective autophagy (Kishnani, Nicolino et al. 2006; Hawes, Kennedy et al. 2007; Kishnani, Corzo et al. 2007; Raben, Takikita et al. 2007).

ERT with rhGAA is the only definitive treatment for Pompe disease. This therapy is often complicated by immune responses to the enzyme which can block efficacy and cause severe adverse outcomes by formation of anti-rhGAA antibodies.

It has been shown that CRIM status carries significant prognostic value in treatment response. Relative to most CRIM-positive patients, CRIM-negative patients tend to do poorly with regard to response to ERT. In CRIM-negative patients, there exist two deleterious GAA mutations that result in no production of native enzyme. Concurrent with clinical decline, persistently elevated anti-rhGAA IgG antibody titers have been seen in CRIM-negative patients while titers for most CRIM-positive patients remained relatively low in comparison (Kishnani, Goldenberg et al. 2009). However, there is a subset of CRIM-positive patients (infants, juveniles and adults) who also develop high sustained anti-rhGAA antibody titers and have a poor clinical outcome. (Banugaria et al. 2011) That CRIM-negative patients generate antibody responses that are unremitting and abrogate the efficacy of a life-saving therapeutic has required the development of clinical protocols to induce tolerance. These protocols and variations thereof are ideally implemented prophylactically or simultaneously with the onset of treatment and before the development of untoward levels of antibody titers against the therapy.

Tolerance-inducing therapies have been explored in experimental animal models and are being implemented for patients who have developed or have a high risk of developing life-threatening antibody response to ERT.

For ongoing antibody responses in the CRIM-negative Pompe setting, in which nephrotic syndrome may be induced by continued administration of enzyme, and which if treated with ERT alone results in clinical decline and death, tolerance-inducing therapies have a favorable risk-benefit ratio. However, in this situation, the immune suppression may be even more intensive and extensive because antibody levels must be markedly reduced to reverse/prevent further clinical deterioration and complications such as nephrotic syndrome and to facilitate tolerance induction. When ERT fails as a result of antibodies, and patient outcome is death or severe disability or impairment (such as ventilator dependency), vigorous therapeutic efforts at eliminating immunity based on the best available experimental and clinical studies is warranted (Wang, Lozier et al. 2008). At this time, there is no agent that has shown success in reducing antibody titers once a patient has high and or persistent antibody titers.

Therapies to trigger inhibitory FcR expressed on B cells and antigen-presenting cells and to target B-cell survival and activation factors (such as B-cell activating factor and B-lymphocyte stimulator) are under development. Depleting approaches using rituximab, a chimeric monoclonal antibody with human IgG1 constant domains that depletes mature B cells expressing the CD20 molecule, can be of use in the prophylaxis setting, potentially allowing introduction of enzyme at a stage when immature enzyme-specific pre- and pro-B cells can be deleted or rendered nonresponsive. Combinations of rituximab and antibodies to B-cell activating factor continue to be of interest (Wang, Lozier et al. 2008). Immune modulation with the anti-CD20 monoclonal antibody rituximab plus methotrexate and intravenous gamma globulin in a CRIM-negative patient has resulted in tolerance induction (Mendelsohn, Messinger et al. 2009). However, this patient did not have high sustained antibody titer at the start of treatment. More difficult than inducing tolerance in a naive setting is the task of reversing an ongoing robust immune response. Studies suggest that rituximab interrupts the pathways driving development of plasma cells and that not all plasma cells have an equally long life span. However, it is not clear whether true tolerance is induced in these settings. Notably lacking from the therapeutic armamentarium are antibodies to target long-lived plasma cells, the elimination of which may be vital in reversing entrenched immune responses (Wang, Lozier et al. 2008). Treatment with rituximab in kidney transplant patients as well as in other disease where high amounts of antibodies are formed against the donor tissue or protein, failed to decrease the antibody titers in those patients. (Everly, Everly et al. 2008).

Gene therapy with vectors (viral or non-viral) is sometimes complicated because of an immune response against the vector carrying the gene. The plasmids used for nonviral gene therapy, alone or in combination with liposomes or electrotransfer, can stimulate immune responses (Bessis, GarciaCozar et al. 2004). Viral vectors are the most likely to induce an immune response, especially those, like adenovirus and adeno-associated virus (AAV), which express immunogenic epitopes within the organism. (Bessis, GarciaCozar et al. 2004). Various viral vectors are used for gene therapy, including but not limited to retroviruses for X-linked severe combined immunodeficiency (X-SCID), adenoviruses for various cancers, adeno-associated viruses (AAVs) to treat muscle and eye disease, lentivirus, herpes simplex virus in nervous system. Anytime a viral vector is introduced into human tissues, the immune system reacts against the vector. The risk of stimulating the immune system in a way that reduces gene therapy effectiveness is always a possibility. Furthermore, the immune system's enhanced response to vectors that it has seen before makes it difficult for gene therapy to be repeated in patients. Furthermore, in general, population antibodies against AAV are formed because of natural exposure and results in antibodies from all four IgG subclasses whereby AAV vector mediated gene therapy in these patients makes it difficult to get a desired response (Boutin, Monteilhet et al. 2010).

Also with gene-therapy, antibodies are formed against the actual protein produced by gene-therapy and these antibodies can reduce efficacy. For example, in a Pompe disease knock-out mouse model (GAA-KO), treatment with AAV2/8 (adeno associated virus vector) containing hGAA under the control of CMV enhancer/chicken B-actin (CB) promotor (AAV-CBhGAApA) resulted in enzyme production in various tissues but this therapy was complicated by high antibody production against the enzyme produced by the gene (Franco, Sun et al. 2005). Immunomodulatory gene therapy in the naïve setting (before the exposure with enzyme replacement therapy) with AAV-LSPhGAApA induces immune tolerance in GAA knock-out mice and regulatory T cells (Treg) were demonstrated to play a role in the tolerance induced by gene therapy (Franco, Sun et al. 2005; Sun, Bird et al. 2007) (see also Sun et al. 2010) but it failed to do so in a setting where significant immune-response had already taken place (as evident by presence of high antibody titers) as described in Example 1 below. This vector therapy could be acting by its possible mechanism on Treg cells but it could be possibly compromised in inducing immune tolerance because of pre-existing plasma cells which continue to produce antibodies.

Immunity against vectors and their contents can substantially reduce the efficiency of gene therapy. A strong immune response against the constituents of the vector or the transgene leads to rejection of the cells infected by the vector and, therefore, to a reduction in the duration of expression of the therapeutic protein (Manno et al. 2006).

Bortezomib is a proteasome inhibitor that acts against both short-lived and long-lived plasma cells. It is FDA approved for the treatment of plasma cell derived tumors—multiple myeloma. Everly et al demonstrated the first clinical use of bortezomib as an anti-humoral agent in treating mixed antibody-mediated rejection (AMR) and acute cellular rejection (ACR). It provided the effective treatment of AMR and ACR with minimal toxicity and sustained reduction of antibodies. The activity of bortezomib against mature, antibody-secreting plasma cells underlies its efficacy in suppressing antibodies by eliminating the source of antibody production (Everly, Everly et al. 2008). Because of extensive immunoglobulin production by plasma cells, proteasome inhibition induces plasma cell depletion as a result of activation of the terminal unfolded protein response (UPR). Late inhibition of anti-apoptotic transcription factor NF-kB may contribute to bortezomib induced plasma cell death (Neubert, Meister et al. 2008).

The present invention provides a method of reducing/preventing antibody titers and/or providing clinical benefit to patients undergoing protein (e.g., enzyme) replacement therapy (PRT). The invention results, at least in part, from studies demonstrating that the proteasome inhibitor, bortezomib, decreases antibody titers by eliminating the source of antibody titer formation, that is, long- and short-lived plasma cells. The invention also relates to methods of reducing antibody titers or preventing the formation of antibody titers and/or for clinical benefit in other settings (including gene therapy) where antibodies complicate therapeutic goals.

SUMMARY OF THE INVENTION

The present invention relates generally to a method of preventing the formation or reducing antibody titers. In one embodiment, the invention relates to a method of preventing or reducing antibody titers in patients undergoing PRT or other therapy involving the administration of a proteinaceous therapeutic agent. The invention also finds application in gene replacement therapy, or other therapeutic modality or modalities (used alone or in combination) involving the administration of exogenous substances for potential therapeutic benefit. The invention further relates to compounds and compositions suitable for use in such methods.

Objects and advantages of the present invention will be clear from the description that follows.

DETAILED DESCRIPTION OF THE INVENTION

Figure 1:
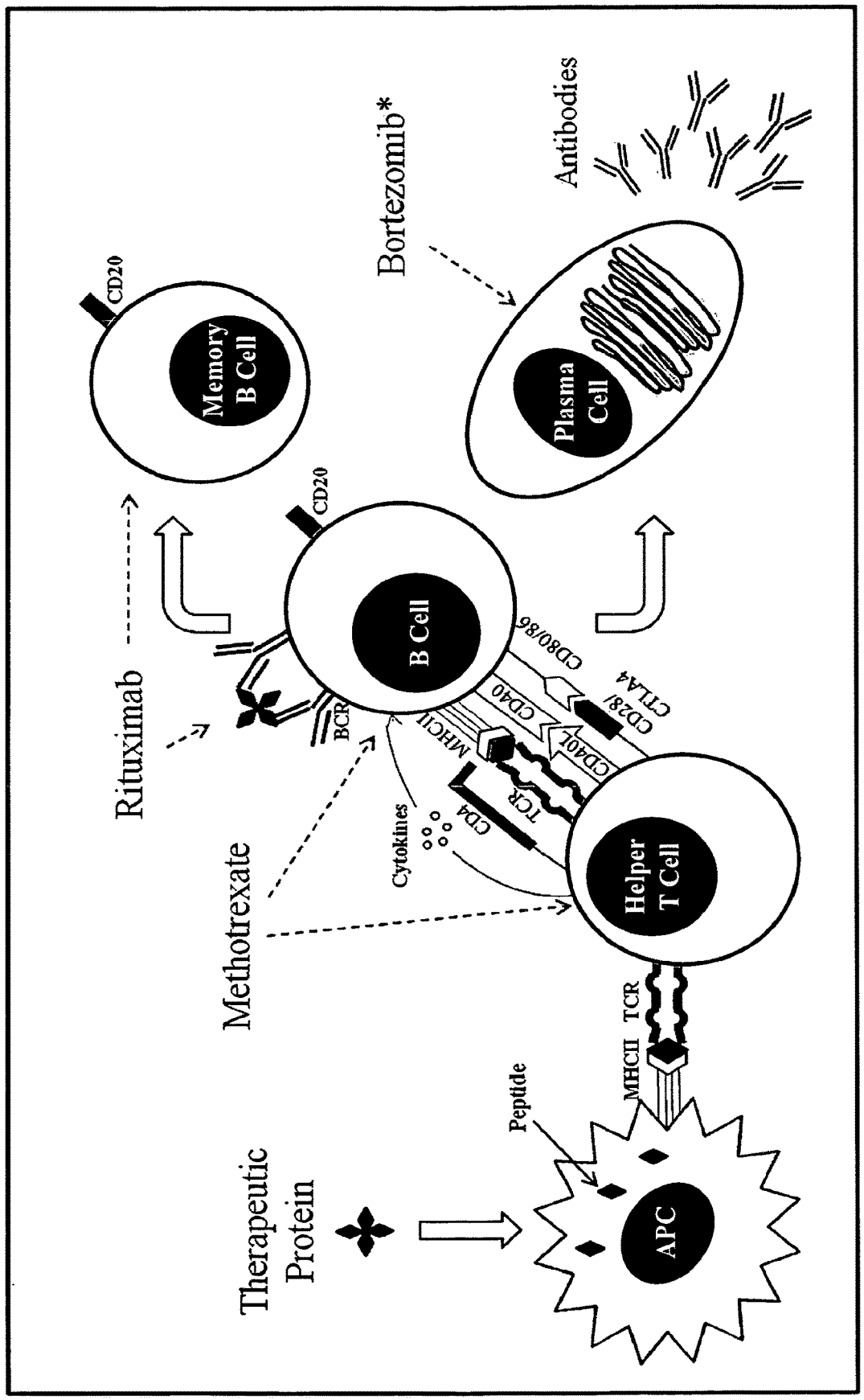
FIG. 1. A simplified, conceptual diagram of a humoral immune response to a therapeutic protein and targets of various immunomodulatory agents. Immune modulation with rituximab (anti-CD20 monoclonal antibody), plus methotrexate and intravenous gamma globulin (WIG) in infantile CRIM negative Pompe patients has resulted in tolerance induction in the naïve setting or after early detection of an antibody response to rhGAA, but prior to the development of high sustained antibody titers (HSAT). Neither rituximab nor methotrexate depletes long-lived plasma cells, the source of such sustained antibody responses. Bortezomib acts against both short- and long-lived plasma cells as a result of activation of the terminal unfolded protein response (UPR) as well as late inhibition of anti-apoptotic transcription factor NF-kB inducing apoptosis of plasma cells (Neubert et al, Nat. Med. 14(7):748-755 (2008)) *Effects of bortezomib are not necessarily limited to those depicted in the figure; APC—antigen presenting cell, TCR—T cell receptor, BCR—B cell receptor.

The present invention relates, at least in part, to a method of reducing antibody titers (or preventing the formation of antibody titers) in patients undergoing protein replacement therapy (PRT), gene replacement therapy with viral or non-viral vector(s), or other therapeutic modality or modalities (used alone or in combination) involving the administration of exogenous substances for potential therapeutic benefit. The invention also finds application in settings where a vector-derived or -associated material (e.g., a protein or other macromolecular product of a vector-encoded transgene) may arise endogenously as a result of related therapy or therapies and elicit an immune response.

In particular, the method described herein applies to any human disease or condition wherein a robust, or otherwise adverse, immune response toward exogenous ("therapeutic") protein or vector therapy induces an elevation of antibody titers to such an extent that such elevation actually or potentially compromises patient health or treatment, including the potential benefit derived from continued treatment with PRT or vector therapy. The method presented herein also applies to patients who may have normal or non-elevated antibody titers prior to any implementation of the method but who may nonetheless be at risk of developing high titers at a future time point. Such patients include, for example, those recently commencing PRT or vector therapy and so-called treatment naïve patients who have yet to receive such therapy or therapies.

In accordance with one aspect of the present invention, a proteasome inhibitor that induces plasma cell depletion is administered to a patient undergoing PRT and in whom an immune response to the therapeutic protein has been established. The proteasome inhibitor is administered in an amount and under such conditions to make it possible to achieve a reduction in antibodies specific for the therapeutic protein and/or vector and/or protein product of gene therapy. Patients commencing or undergoing PRT who are at risk of developing an immune response to the therapeutic protein and/or vector and/or protein product of gene therapy, as outlined above, are also suitable subjects for treatment with proteasome inhibitors in accordance with the method of the present invention. Other immunomodulating agents can be used in combination with proteasome inhibitor at the time, prior to or after the administration of proteasome inhibitor for reduction/prevention of formation of antibody titers or for clinical benefit in such disorders.

Preferred proteasome inhibitors are disclosed, for example, in U.S. Pat. No. 7,531,526 (incorporated in its entirety by reference) and have the formula (1a):

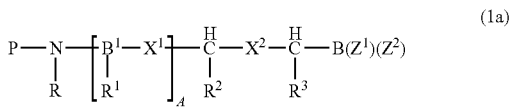

(1a)

or a pharmaceutically acceptable salt thereof,
wherein
P is hydrogen or an amino-group-protecting moiety (the term "amino-group-protecting moiety," as used herein, refers to terminal amino protecting groups that are typically employed in organic synthesis, especially peptide synthesis; any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl (see, for example, The Peptides, Gross and Mienhoffer, eds., Academic Press, New York (1981), Vol. 3, pp. 3-88; and Green, T. W. & Wuts, P. G. M., Protective Groups in Organic Synthesis, 2$^{nd}$ edition, John Wiley and Sons, Inc., New York (1991)), preferred protecting groups include aryl-, aralkyl-, heteroaryl- and heteroarylalkyl-carbonyl and sulfonyl moieties);

$B^1$, at each occurrence, is independently one of N or CH;
$X^1$, at each occurrence, is independently one of —C(O)—NH—, —CH$_2$—NH—, —CH(OH)—CH$_2$—, —CH(OH)—CH(OH)—, —CH(OH)—CH$_2$—NH—, —CH═CH—, —C(O)—CH$_2$—, —SO$_2$—NH—, —SO$_2$CH$_2$— or —CH(OH)—CH$_2$—C(O)—NH—, provided that when $B^1$ is N, then $X^1$ attached to $B^1$ is —C(O)—NH;

$X^2$ is one of —C(O)—NH—, —CH(OH)—CH$_2$—, —CH(OH)—CH(OH)—, —C(O)—CH$_2$—, —SO$_2$—NH—, —SO$_2$—CH$_2$— or —CH(OH)—CH$_2$—C(O)—NH—;

R is hydrogen or alkyl or R forms together with the adjacent $R^1$, or when A is zero, forms together with the adjacent $R^2$, a nitrogen-containing mono-, bi- or tricyclic, saturated or partially saturated ring system having 4-14 ring members, that can be optionally substituted by one or two of keto, hydroxy, alkyl, aryl, aralkyl, alkoxy or aryloxy;

$R^1$, at each occurrence, is independently one of hydrogen, alkyl, cycloalkyl, aryl, a 5-10 membered saturated, partially unsaturated or aromatic heterocycle or —CH$_2$—R$^5$, where the ring portion of any of said aryl, aralkyl, alkaryl or heterocycle can be optionally substituted;

$R^2$ is one of hydrogen, alkyl, cycloalkyl, aryl, a 5-10 membered saturated, partially unsaturated or aromatic heterocycle or —CH$_2$—R$^5$, where the ring portion of any of said aryl, aralkyl, alkaryl or heterocycle can be optionally substituted;

$R^3$ is one of hydrogen, alkyl, cycloalkyl, aryl, a 5-10 membered saturated, partially unsaturated or aromatic heterocycle or —CH$_2$—R$^5$, where the ring portion of any of said aryl, aralkyl, alkaryl or heterocycle can be optionally substituted;

$R^5$, in each instance, is one of aryl, aralkyl, alkaryl, cycloalkyl, a 5-10 membered saturated, partially unsaturated or aromatic heterocycle —W—R$^6$, where W is a chalcogen and $R^6$ is alkyl, where the ring portion of any of said aryl, aralkyl, alkaryl or heterocycle can be optionally substituted;

$Z^1$ and $Z^2$ are independently alkyl, hydroxy, alkoxy, aryloxy, or $Z^1$ and $Z^2$ form a moiety derived from a dihydroxy compound having at least two hydroxy groups separated by at least two connecting atoms in a chain or ring, said chain or ring comprising carbon atoms, and optionally, a heteroatom or heteroatoms which can be N, S, or O; and A is 0, 1, or 2.

Other novel boronic acid and ester derivatives include compounds having a single amino acid side-chain. These compounds have the following formula (2a):

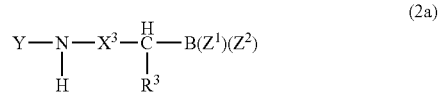

(2a)

and pharmaceutically acceptable salts thereof;
wherein
Y is one of $R^8$—C(O)—, $R^8$—NH—C(O)— or $R^8$—O—C(O)—, where $R^8$ is one of alkyl, aryl, alkaryl, aralkyl, any of which can be optionally substituted, or when Y is $R^8$—C(O)— or $R^8$—SO$_2$—, then $R^8$ can also be an optionally substituted 5-10 membered, saturated, partially unsaturated or aromatic heterocycle;

$X^3$ is a covalent bond or —C(O)—CH$_2$—;

$R^3$ is one of hydrogen, alkyl, cycloalkyl, aryl, a 5-10 membered saturated, partially unsaturated or aromatic heterocycle or —CH$_2$—R$^5$, where the ring portion of any of said aryl, aralkyl, alkaryl or heterocycle can be optionally substituted;

$R^5$, in each instance, is one of aryl, aralkyl, alkaryl, cycloalkyl, a 5-10 membered saturated, partially unsaturated or aromatic heterocycle or —W—R$^6$, where W is a chalcogen and $R^6$ is alkyl, where the ring portion of any of said aryl, aralkyl, alkaryl or heterocycle can be optionally substituted; and $Z^1$ and $Z^2$ are independently alkyl, hydroxy, alkoxy, aryloxy, or together form a moiety derived from dihydroxy compound having at least two hydroxy groups separated by at least two connecting atoms in a chain or ring, said chain or ring comprising carbon atoms, and optionally, a heteroatom or heteroatoms which can be N, S, or O;

provided that when Y is $R^8$—C(O)—, $R^8$ is other than phenyl, benzyl or C$_1$-C$_3$ alkyl.

Alternatively, the group Y in formula (2a) above, can be:

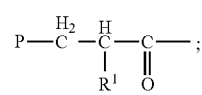

P is one of $R^7$—C(O)—, $R^7$—SO$_2$—, $R^7$—NH—(O)— or $R^7$—O—C(O)—;

R⁷ is one of alkyl, aryl, alkaryl, aralkyl, any of which can be optionally substituted, or when Y is R⁷—C(O)— or R⁷—SO₂—, R⁷ can also be an optionally substituted 5-10 membered saturated, partially unsaturated or aromatic heterocycle; and R¹ is defined above as for formula (1a).

Proteasome inhibitors of formula (1b) suitable for use include:

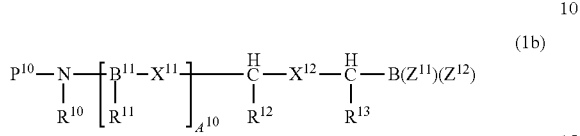

or a pharmaceutically acceptable salt thereof;
wherein
P¹⁰ is hydrogen or an amino-group-protecting moiety;
B¹¹ is independently one of N or CH;
X¹¹, at each occurrence, is independently one of —C(O)—NH—, —CH₂—NH—, —CH(OH)—CH₂, —CH(OH)—CH(OH)—, —CH(OH)—H₂—NH—, —CH═CH—, —C(O)—CH₂—, —SO₂—NH—, —SO₂—CH₂— or —CH(OH)—CH₂—C(O)—NH—, provided that when B¹¹ is N, then X¹¹ is —C(O)—NH;
X¹² is one of —C(O)—NH—, —CH(OH)—CH₂—, —CH(OH)—CH(OH)—, —C(O)—CH₂—, —SO₂—NH—, —SO₂—CH₂— or CH(OH)—CH₂—C(O)—NH—;
R¹⁰ is hydrogen or alkyl, or R¹⁰ forms together with the adjacent R¹¹, or when A¹⁰ is zero, forms together with the adjacent R¹², a nitrogen containing mono-, bi- or tricyclic, saturated or partially saturated ring system having 4-14 ring members, that can be optionally substituted by one or two of keto, hydroxy, alkyl, aryl, aralkyl, alkoxy or aryloxy;
R¹¹, at each occurrence, is independently one of hydrogen, alkyl, cycloalkyl, aryl, a 5-10 membered saturated, partially unsaturated or aromatic heterocycle or —CH₂—R¹⁵, where the ring portion of any of said aryl, aralkyl, alkaryl or heterocycle can be optionally substituted;
R¹² and R¹³ are each independently one of hydrogen, alkyl, cycloalkyl, aryl, a 5-10 membered saturated, partially unsaturated or aromatic heterocycle or —CH₂—R¹⁵, where the ring portion of any of said aryl, aralkyl, alkaryl or heterocycle can be optionally substituted, where R¹⁵ is aryl, aralkyl, alkaryl, cycloalkyl, a 5-10 membered saturated, partially unsaturated or aromatic heterocycle, or -chalcogen-alkyl, where the ring portion of any of said aryl, aralkyl, alkaryl or heterocycle can be optionally substituted;
Z¹¹ and Z¹² are independently alkyl, hydroxy, alkoxy, aryloxy, or Z¹¹ and Z¹² together form a moiety derived from a dihydroxy compound having at least two hydroxy groups separated by at least two connecting atoms in a chain or ring, said chain or ring comprising carbon atoms, and optionally, a heteroatom or heteroatoms which can be N, S, or O, and
A¹⁰ is 0, 1, or 2

Proteasome inhibitors of formula (2b) include:

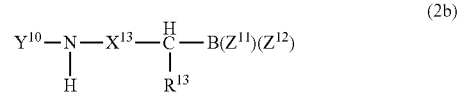

or pharmaceutically acceptable salts thereof;

wherein
Y¹⁰ is one of R⁸—C(O)—, R⁸—SO₂—, R⁸—NH—C(O)— or R⁸—O—C(O)—, where R⁸ is one of alkyl, aryl, alkaryl, aralkyl, any of which can be optionally substituted, or when Y is R⁸—C(O)— or R⁸—SO₂—, then R⁸ can also be an optionally substituted 5-10 membered, saturated, partially unsaturated or aromatic heterocycle;
X¹³ is a covalent bond or —C(O)—CH₂—;
R¹³ is one of hydrogen, alkyl, cycloalkyl, aryl, a 5-10 membered saturated, partially unsaturated or aromatic heterocycle or —CH₂—R¹⁵, where the ring portion of any of said aryl, aralkyl, alkaryl or heterocycle can be optionally substituted;
R¹⁵, in each instance, is one of aryl, aralkyl, alkaryl, cycloalkyl, a 5-10 membered saturated, partially unsaturated or aromatic heterocycle or —W—R¹⁶, where W is a chalcogen and R¹⁶ is alkyl, where the ring portion of any of said aryl, aralkyl, alkaryl or heterocycle can be optionally substituted; and
Z¹¹ and Z¹² are independently alkyl, hydroxy, alkoxy, aryloxy, or together form a moiety derived from a dihydroxy compound having at least two hydroxy groups separated by at least two connecting atoms in a chain or ring, said chain or ring comprising carbon atoms, and optionally, a heteroatom or heteroatoms which can be N, S, or O.

Alternatively, the group Y in formula (2b) can be:

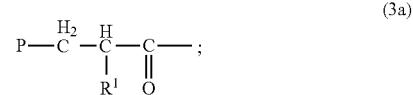

P is one of R⁷—(O)—, R⁷—SO₂—, R⁷—NH—C(O)— or R⁷—O—C(O)—;
R⁷ is one of alkyl, aryl, alkaryl, aralkyl, any of which can be optionally substituted, or when Y is R⁷—C(O)— or R⁷—SO₂—, R⁷ can also be an optionally substituted 5-10 membered saturated, partially unsaturated or aromatic heterocycle; and
R¹ is as defined for formula (1a) above.

Preferred embodiments of the aforementioned methods of use employ compounds of formula (1a) and formula (2a) as defined above.

Examples of suitable proteasome inhibitors include without limitation the following compounds, as well as pharmaceutically acceptable salts and boronate esters thereof: N-(4-morpholine)carbonyl-β-(1-naphthyl)-L-alanine-L-leucine boronic acid, N-(8-quinoline)sulfonyl-β-(1-naphthyl)-L-alanine-L-leucine boronic acid, N-(2-pyrazine)carbonyl-L-phenylalanine-L-leucine boronic acid, L-proline-L-leucine boronic acid, N-(2-quinoline)carbonyl-L-homophenylalanine-L-leucine boronic acid, N-(3-pyridine)carbonyl-L-phenylalanine-L-leucine boronic acid, N-(3-phenylpropionyl)-L-phenylalanine-L-leucine boronic acid, N-(4-morpholine)carbonyl-L-phenylalanine-L-leucine boronic acid, N-(4-morpholine)carbonyl-(O-benzyl)-L-tyrosine-L-leucine boronic acid, N-(4-morpholine)carbonyl-L-tyrosine-L-leucine boronic acid, and N-(4-morpholine)carbonyl-[0-(2-pyridylmethyl)]-L-tyrosine-L-leucine boronic acid.

The proteasome inhibitors can be used in vitro or in vivo. They can be administered by any number of known routes, including orally, intravenously, intramuscularly, subcutaneously, intrathecally, topically, and by infusion (Platt et al., U.S. Pat. No. 4,510,130; Badalamente et al., Proc. Natl. Acad. Sci. U.S.A. 86:5983-5987 (1989); Staubli et al., Brain Research 444:153-158 (1988)) and will generally be administered in combination with a physiologically acceptable carrier (e.g., physiological saline). The effective quantity of inhibitor given will be determined empirically and will be based on such considerations as the particular proteasome inhibitor used, the condition of the individual, and the size and weight of the individual. It is to be expected that the general end-use application dose range will be about 0.01 to 100 mg per kg per day, preferably, 0.1 to 75 mg per kg per day for an effective therapeutic effect.

Particularly preferred for use in the invention is bortezomib (VELCADE®), the monomeric boronic acid [(1R)-3-methyl-1-[[(2S)-1-oxo-3-phenyl-2-[(pyrazinylcarbonyl)amino]propyl]amino]butyl]boronic acid having the structure:

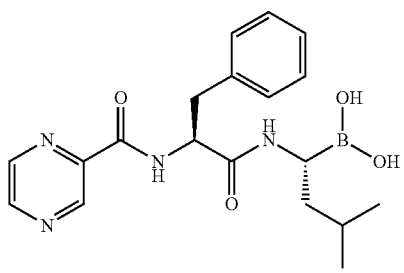 [SMILES: CC(C)C[C@H](NC(=O)[C@H](Cc1ccccc1)NC(=O)c1cnccn1)B(O)O]

Figure 2A:
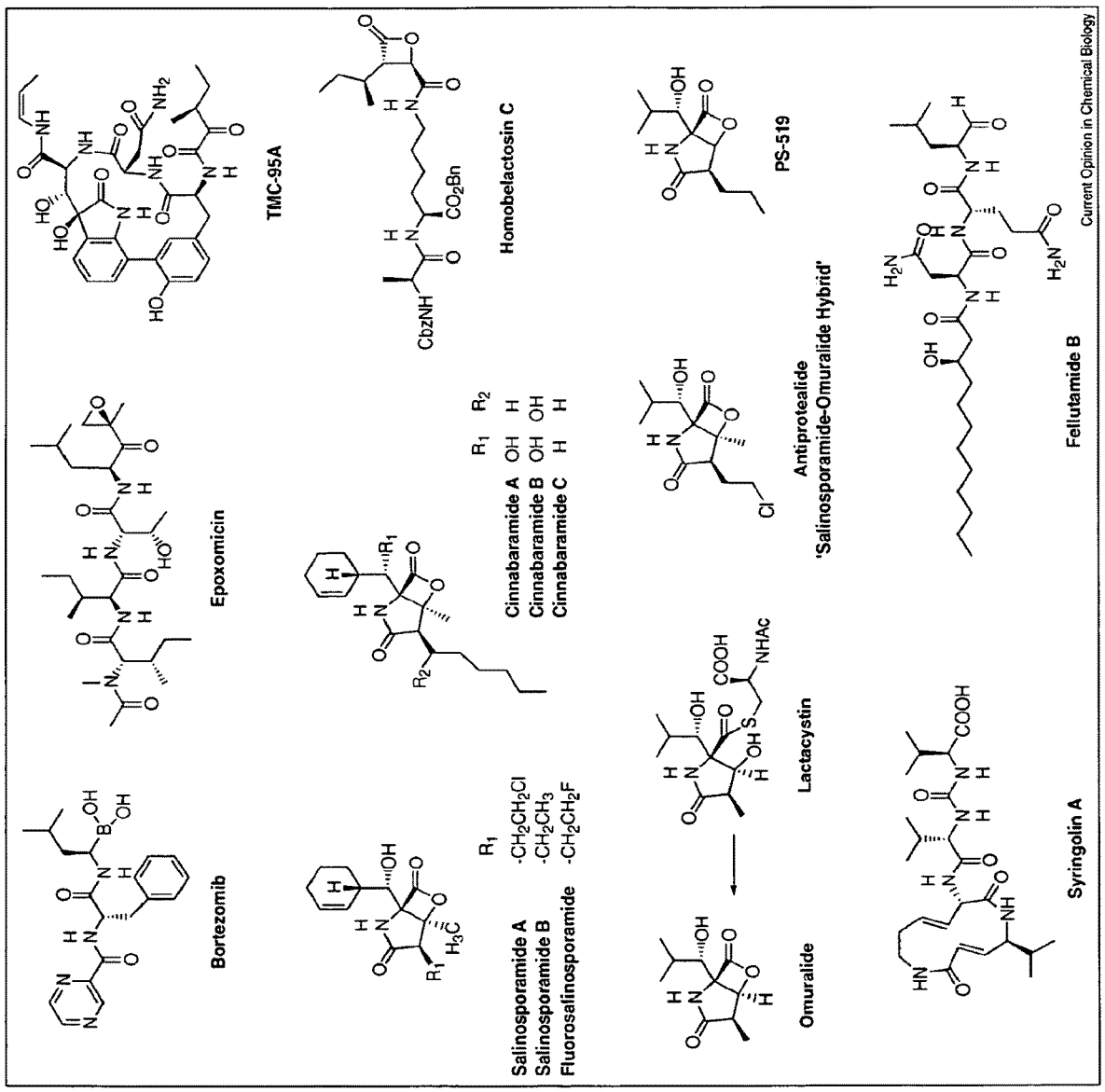
FIGS. 2A-2B. Representative structures of proteasome inhibitors.
Figure 2B:
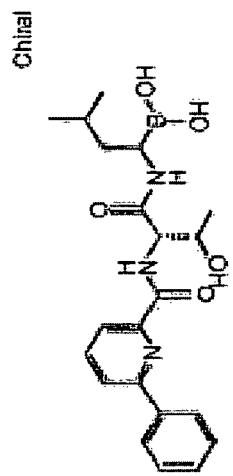
Figure 2B:
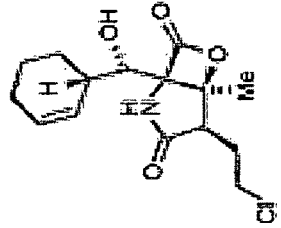
Figure 2B:
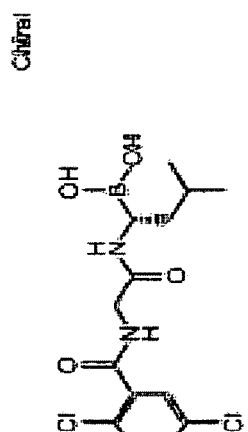
Figure 2B:
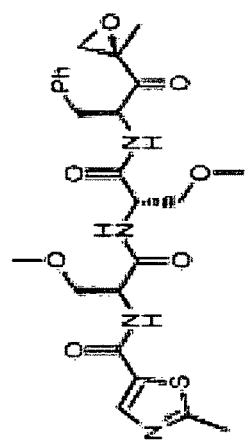
Figure 2B:
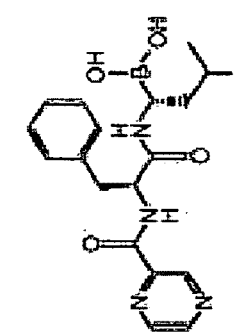
Figure 2B:
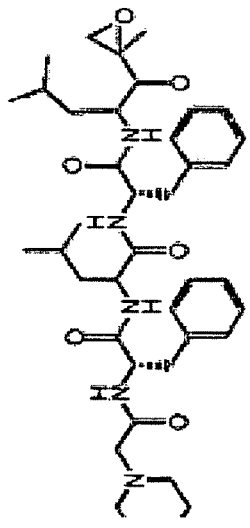
Figure 3A:
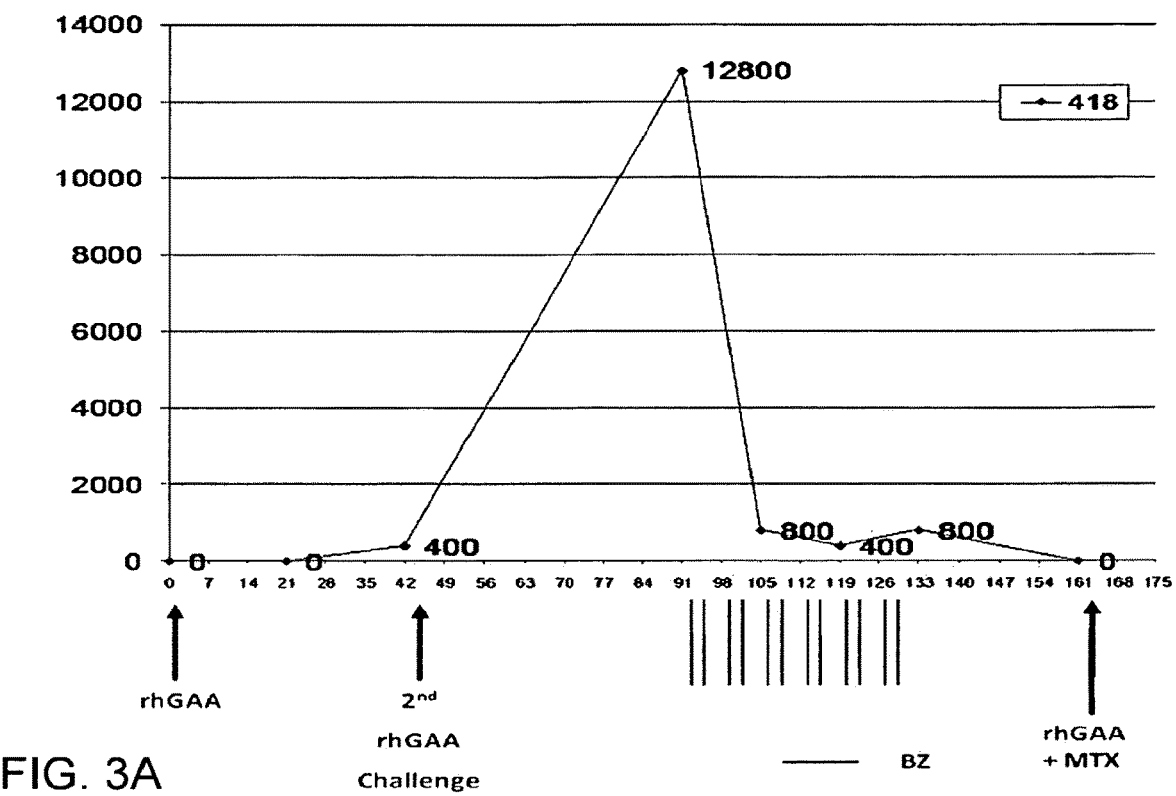
FIGS. 3A-3F. Antibody titers at different time point and treatment schedule in Pompe disease knock-out mouse model.
Figure 3B:
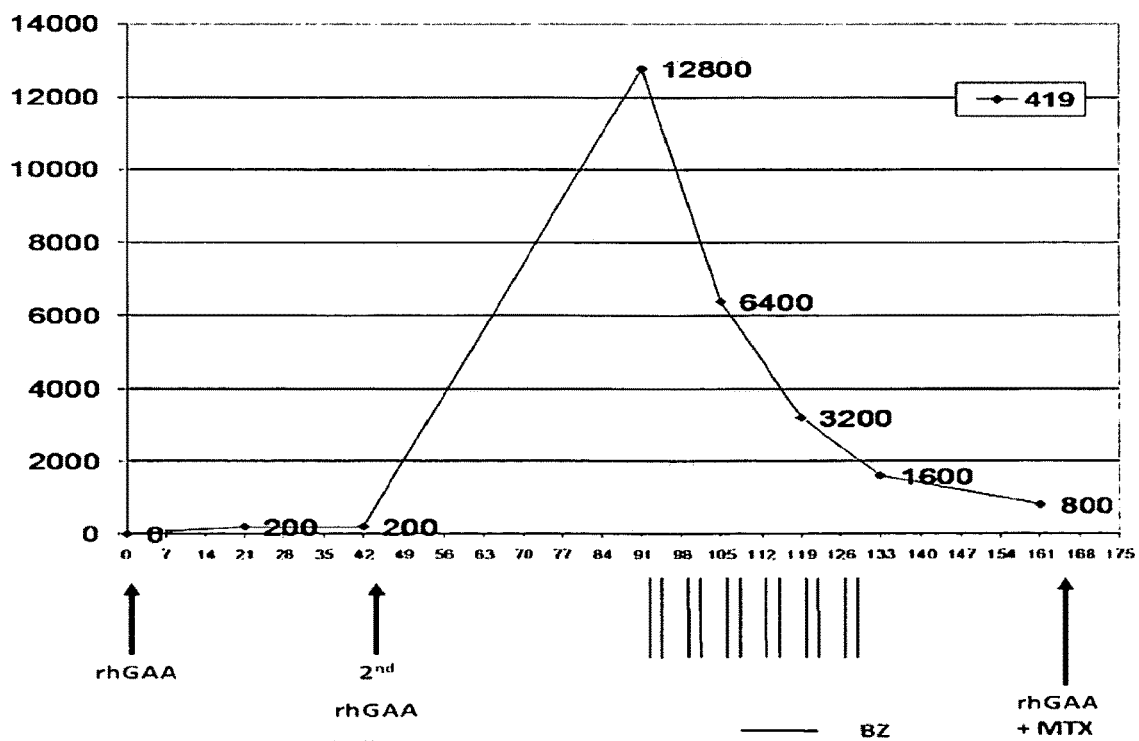
Figure 3C:
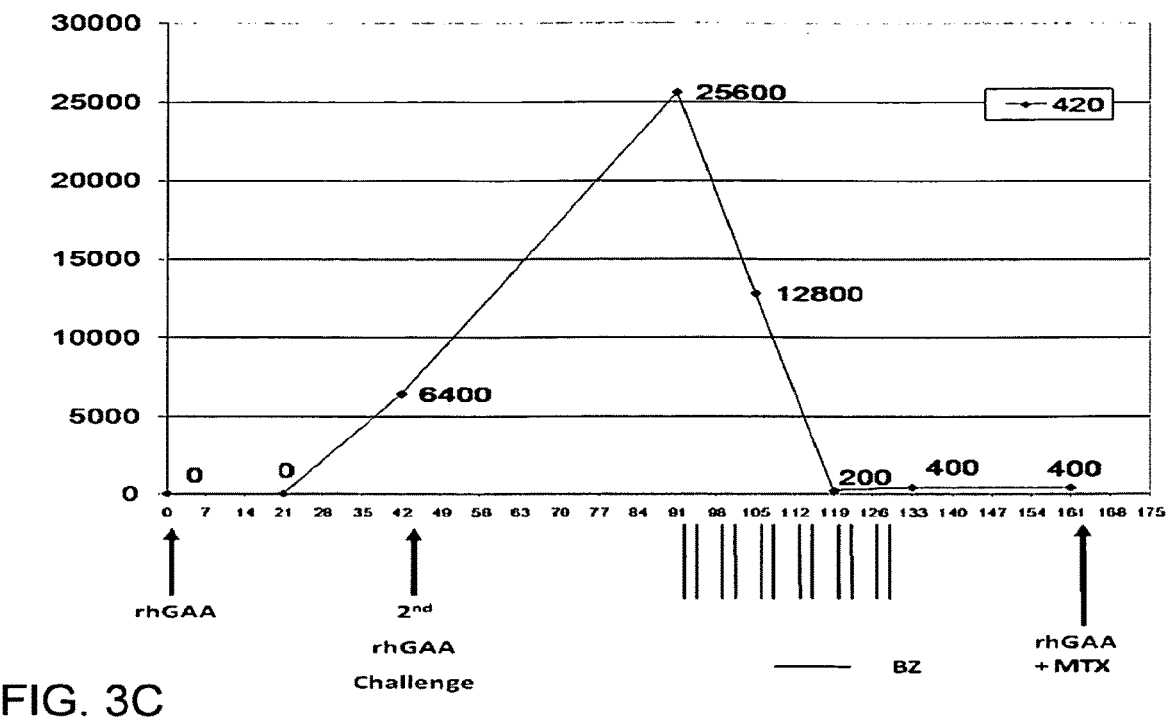
Figure 3D:
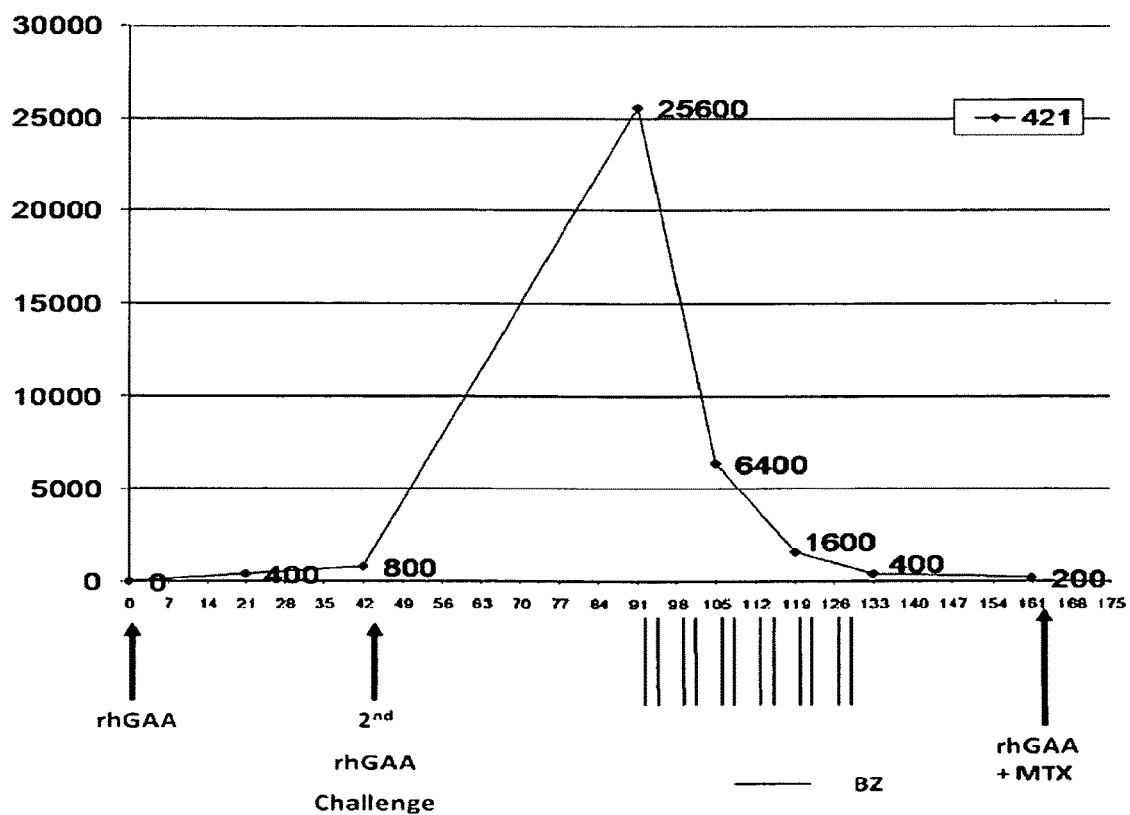
Figure 3E:
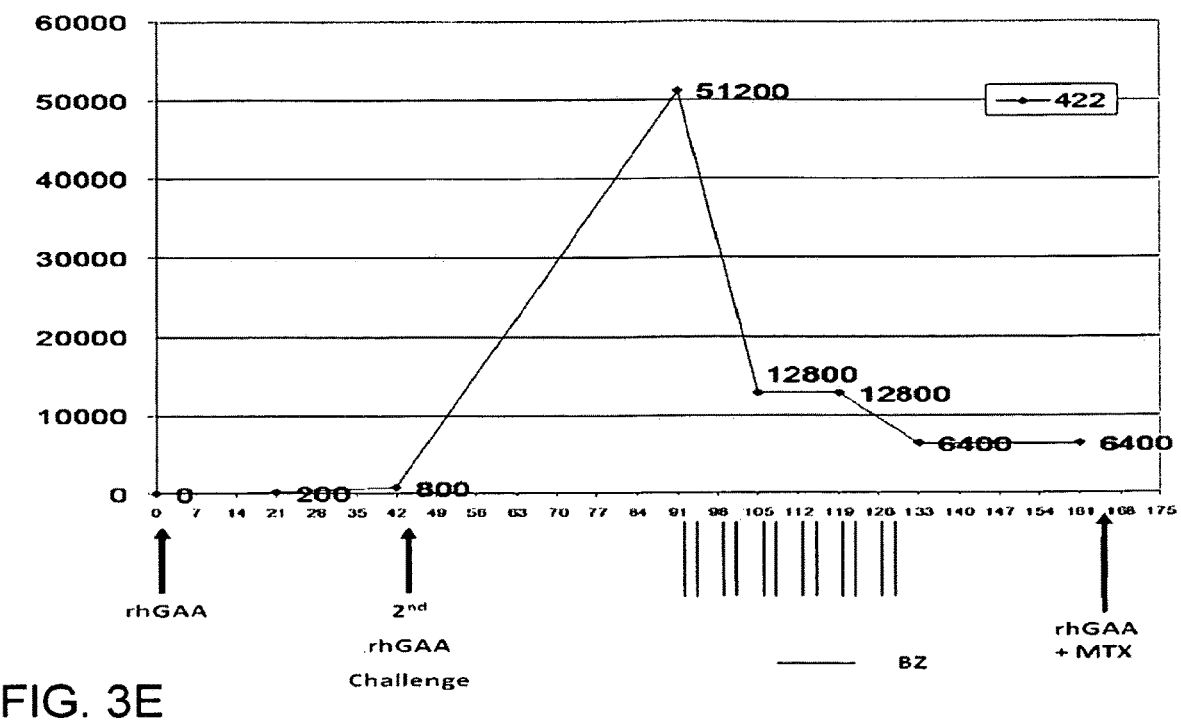
Figure 3F:
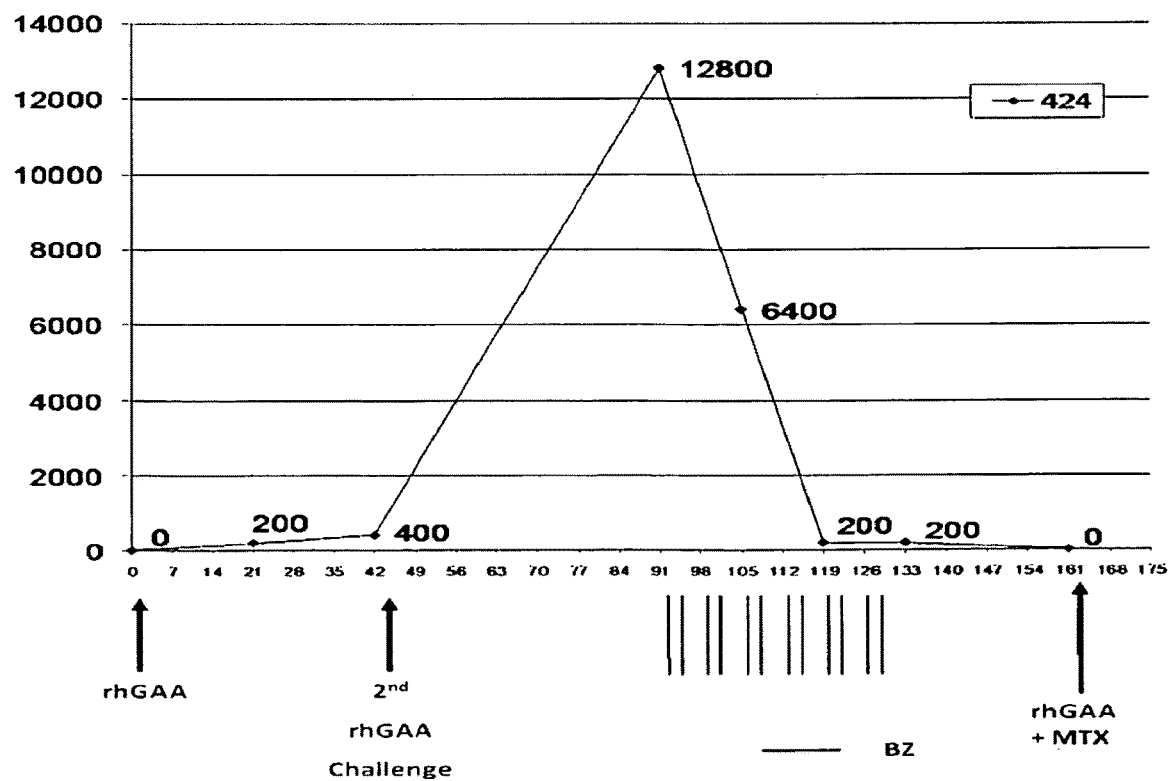

Other proteasome inhibitors suitable for use in the invention include agents currently being evaluated in pre-clinical and clinical trials for the treatment of a multitude of conditions (e.g., FIGS. 2A & 2B; Tables 1 & 2). The invention also includes the use of having known or potential activity against plasma cells through putative mechanism(s) generally distinct from proteasome inhibitors (e.g., MLN4924, Soucy, Smith et al 2009) as a class; this includes the use of combinations of agents, or their derivatives, belonging to the same overall class or subclass of agents (for example, and not necessarily limited to, the use of two or more proteasome inhibitors or two or more NEDD-8 inhibitors or two or more E3 ligase inhibitors) or, alternatively, agents or their derivatives belonging to different classes or subclasses of agent (for example, and not necessarily limited to, the use of one or more proteasome inhibitor with one or more NEDD-8 inhibitors and/or one or more E3 ligase inhibitors) where, in either instance, the combination presents greater potential relative benefit for a given patient and their clinical situation than what may otherwise occur if a single agent were used. This has been borne out to date, for example, in the treatment of prostate cancer where the combination of two proteasome inhibitors was more efficacious than what had hitherto been observed with the use of either agent alone (Shirley, Kaddour-Djebbar et al. 2005). Furthermore, the synergy that was observed between the two agents had the additional benefits of reducing the amount of each drug needed for treatment which, in turn, made it possible for an overall reduction in the side effect profile relative to what is typically observed when either agent is used alone in similar settings (Shirley, Kaddour-Djebbar et al. 2005). While combinations of agents have yet to be described in the context of reducing or preventing antibody titers, it is not unreasonable to assume that such combinations, could find similar application in the context of the methods disclosed herein relating to a reduction or prevention of antibody titers in the context of patients undergoing, or potentially undergoing, PRT, gene replacement therapy, and/or other therapeutic modalities.

TABLE 1

Properties of bortezomib and some other second-generation proteasome inhibitors [adapted from (Dick and Fleming)].

| Proteasome inhibitor | IC$_{50}$ β5/β2/β1 (nM) | IC$_{50}$ NF-κB (nM) | Dissociation t$_{1/2}$ (min) | Stage of clinical development | Route of administration |
|---|---|---|---|---|---|
| Bortezomib | 2.4-7.9/590-4200/24-74 (Kupperman, Lee et al.; Chauhan, Catley et al. 2005; Demo, Kirk et al. 2007) | 36-40 (Kupperman, Lee et al.; Chauhan, Catley et al. 2005; Williamson, Blank et al. 2006) | 110 (Kupperman, Lee et al.) | Approved for MM and MCL | IV (SC also studied) (Moreau, Coiteux et al. 2008) |
| MLN9708 (Kupperman, Lee et al.) | 3.4/3500/31 | 62 | 18 | Phase I | IV (Oral dosing efficacious in vivo) |
| CEP-18770 (Dorsey, Iqbal et al. 2008; Piva, Ruggeri et al. 2008) | 3.8/>100/<100 | NR | NR-slowly reversible | Phase I | IV |
| Carfilzomib (Demo, Kirk et al. 2007) | 6/3600/2400 | NR | Irreversible | Phase II | IV |

TABLE 1-continued

Properties of bortezomib and some other second-generation proteasome inhibitors [adapted from (Dick and Fleming)].

| Proteasome inhibitor | IC$_{50}$ β5/β2/β1 (nM) | IC$_{50}$ NF-κB (nM) | Dissociation t$_{1/2}$ (min) | Stage of clinical development | Route of administration |
|---|---|---|---|---|---|
| PR-047 (Zhou, Aujay et al. 2009) | 36/NR/NR | NR | Irreversible | Preclinical | Orally bioavailable |
| NPI-0052 | 3.5/28/430 (Chauhan, Catley et al. 2005) | 13-20 (Chauhan, Catley et al. 2005; Williamson, Blank et al. 2006) | Irreversible | Phase I | IV |

TABLE 2

Additional examples of proteasome inhibitors currently under development.

| Company Name | Product Name | Phase | Indication | Mode of Action |
|---|---|---|---|---|
| 4SC AG | CEP18770 | D | Cancer | Apoptosis Inducer |
| 4SC AG | 4SC206 | PC | Cancer | — |
| Cephalon Inc | CEP28331 | PC | Multiple Myeloma | Anticancer |
| Laboratoires Pierre Fabre SA | Tetra-acridines PIERRE FABRE | PC | Cancer | Anticancer; DNA Repair Disrupter |
| Onyx Pharmaceuticals Inc. | ONX0912 | PC | Cancer (Hematological and Solid Tumors) | Anticancer |
| Onyx Pharmaceuticals Inc. | ONX0914 | PC | Autoimmune Diseases | Anti-Inflammatory |
| Telik Inc | Proteasome Inhibitor TELIK | PC | Cancer | Anticancer; Apoptosis Inducer |
| EOS S.p.A. | E18770 | I | Cancer | Angiogenesis Inhibitor; Anticancer; Apoptosis Inducer |
| Millennium Pharmaceuticals, Inc. | MLN9708 | I | Cancer (Advanced Malignancies) | Anticancer |
| Takeda Pharmaceutical Company Limited | MLN9708 | I | Cancer (Advanced Malignancies) | Anticancer |
| Cephalon Inc | CEP18770 | II | Cancer | Anticancer; Apoptosis Inducer |
| Onyx Pharmacetuticals, Inc.; Multiple Myeloma Research Foundation (MMRF) | PR171 | II | iple Myeloma (Relapsed and Refractory Multiple Myeloma) | — |
| Onyx Pharmaceuticals Inc | PR171 | II | Solid Tumors (Advanced Solid Tumors) | Anticancer |
| Onyx Pharmaceuticals Inc | PR171 with Lenalidomide and Low Dose Dexamethasone | II | Multiple Myeloma (Relapsed or Refractory Multiple Myeloma) | — |
| 4SC AG | 4SC206 | D | Viral Infections | Apoptosis Inducer |
| Cell Therapeutics Inc | CEP18770 | D | Cancer | Anticancer |
| Onyx Pharmaceuticals Inc | PR171 | D | Lymphoma (Waldenstrom's Macroglobulinemia) | — |
| Peplin, Inc. | NEOSH101 | D | Alopecia (Hair Loss) (Androgenetic Alopecia) | — |
| Peplin, Inc. | NEOSH101 | D | Alopecia (Hair Loss) (Androgenetic Alopecia) | Anticancer; Apoptosis Inducer |

TABLE 2-continued

Additional examples of proteasome inhibitors currently under development.

| Company Name | Product Name | Phase | Indication | Mode of Action |
| --- | --- | --- | --- | --- |
| Jeil Pharmaceutical Co., Ltd. | Proteasome inhibitor JEIL | NA | Cancer | Anticancer |
| Onyx Pharmaceuticals Inc | Immunoproteasome Specific Inhibitor PROTEOLIX | NA | Hematological Malignancies (Hematological Cancers) | — |

Figure 6A:
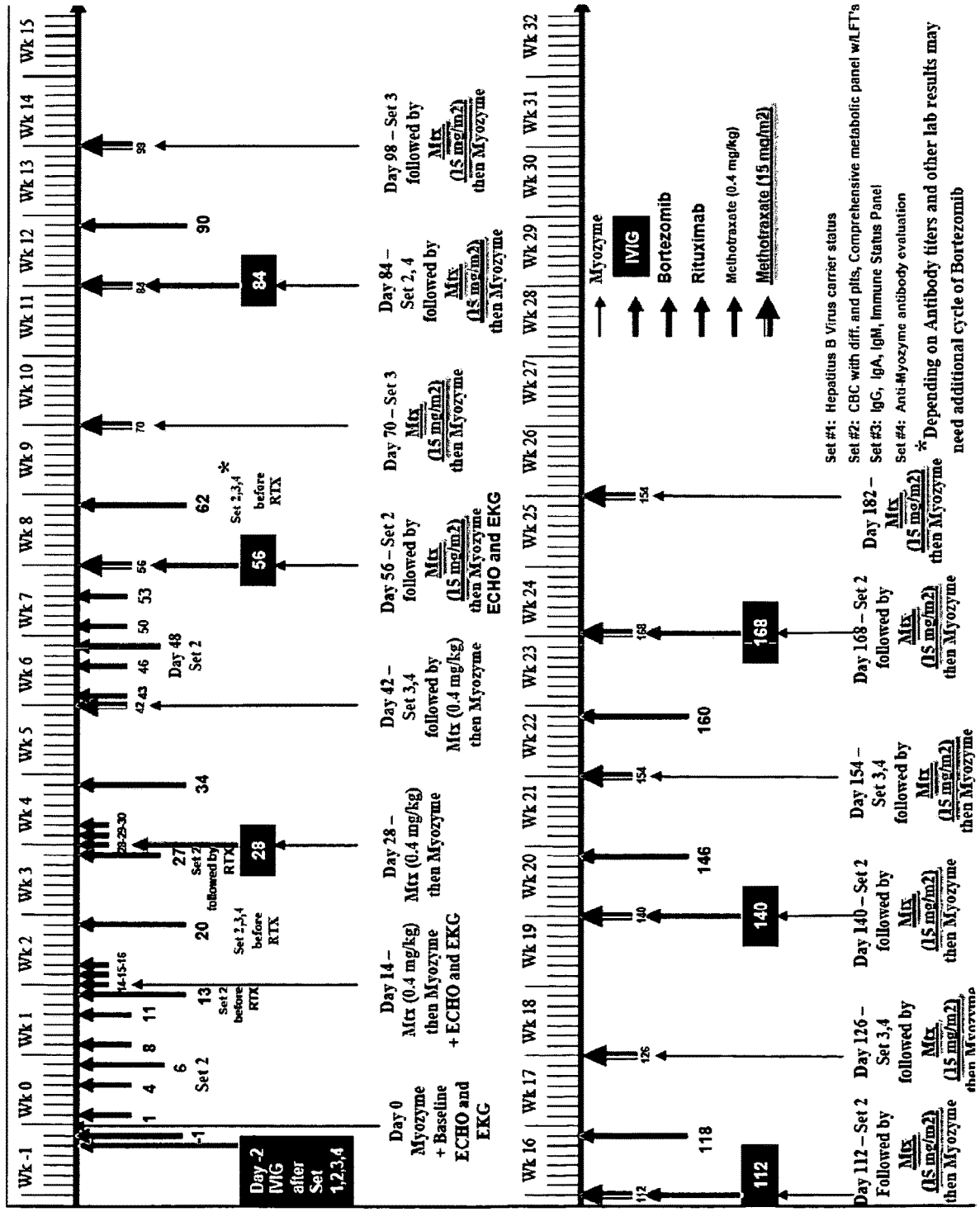
FIGS. 6A and 6B. Immune modulation timelines.
Figure 6B:
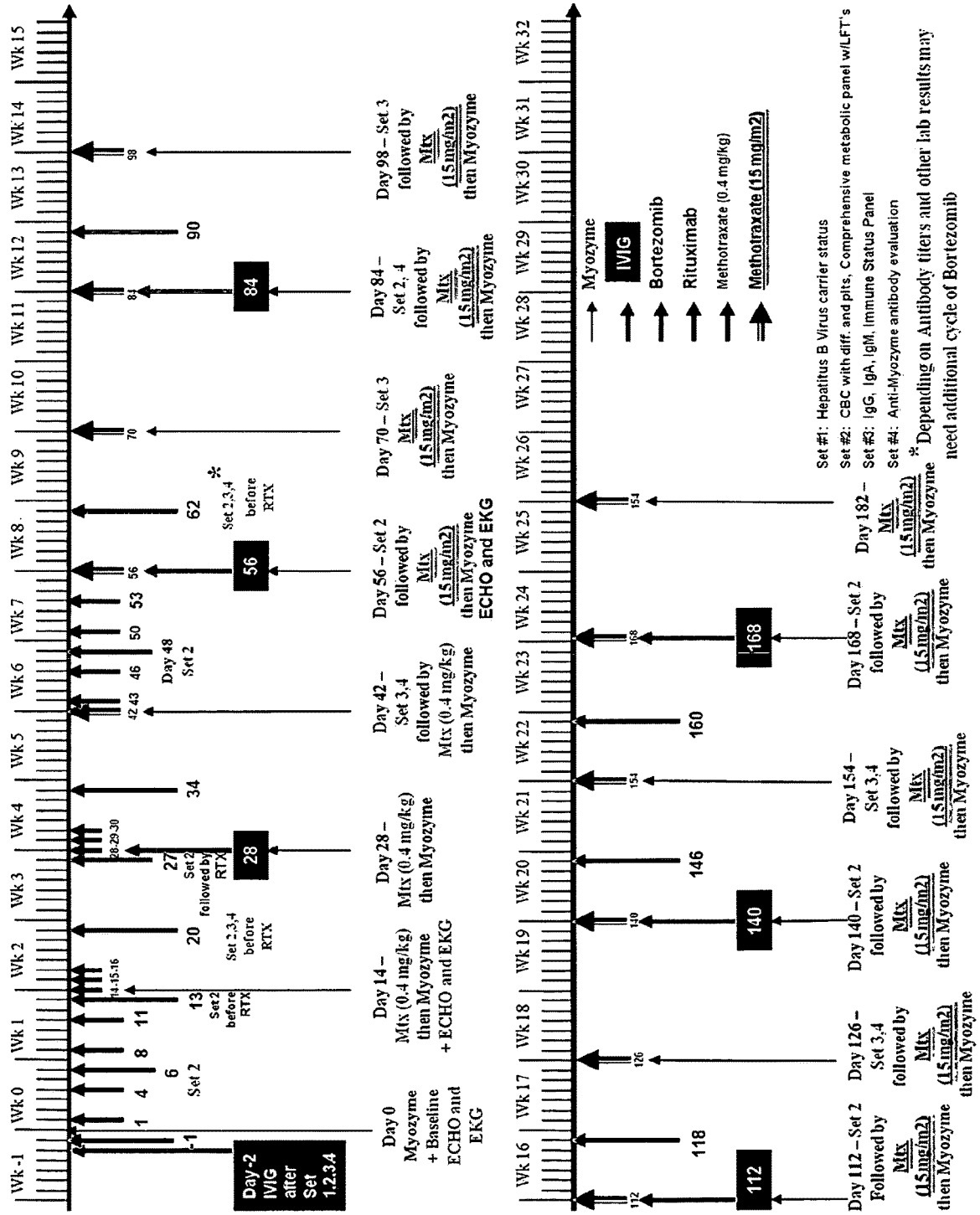

Optimum dosing regimens of proteasome inhibitors can be determined by one skilled in the art and can vary with the proteasome inhibitor, the patient and the effect sought. For example, the inhibitor can be administered intravenously in an amount of 0.01 mg/m$^2$ to 200 mg/m$^2$, preferably 0.01 mg/m$^2$ to 2 mg/m$^2$, more preferably 0.6 mg/m$^2$ to 1.5 mg/m$^2$, with various dosing schedules which may involve, for example, twice weekly dosing. The proteasome inhibitor can also be administered through other routes including but not limited to orally, subcutaneously, intramuscularly, intrathecally, intraperitoneally in doses generally ranging from 0.01 mg/m$^2$ to 200 mg/m$^2$, preferably 0.01 mg/m$^2$ to 2 mg/m$^2$, more preferably 0.6 mg/m$^2$ to 1.5 mg/m$^2$. Optimal dosing of proteasome inhibitors may take into account such considerations as the desired dosing schedule(s) and the bioavailability of the drug for a given route(s) of administration and guided by the clinical and laboratory parameters of the patient at any particular time. (Exemplary dosing strategies are set forth in FIG. 6.)

As described above, adverse effects of anti-rhGAA antibodies have been observed in Pompe disease patients undergoing ERT with Myozyme®. Adverse effects of antibodies have also been described for mucopolysaccharidosis (MPS) I, another lysosomal storage disorder that primarily affects the connective tissue. In a canine MPS I model, the formation of antibodies influences the efficacy of recombinant a-L-iduronidase. Uptake of a-L-iduronidase by MPS I fibroblasts was especially reduced in the presence of high titers of antibodies. Interestingly, the enzyme was mistargeted to organs containing a high number of phagocytes, suggesting uptake of immune complexes by the macrophages. Institution of immunosuppressive treatment using cyclosporine A was hypothesized to promote a state of tolerance, as reflected by a reduction in antibody titers over time in MPS I dogs receiving a-L-iduronidase; experiments subsequently revealed that these dogs had an improved response to enzyme replacement therapy with a-L-iduronidase (Kakkis et al 2004; Dickson et al 2008). In this instance, however, cyclosporine A was being used for the purposes of immunetolerance induction and in a manner less specific (i.e., no direct targeting of the ultimate source of antibodies, plasma cells) than the method of treatment described herein, which relates to the use of proteasome inhibitors for the prevention or reduction of antibodies in patients undergoing, for example, enzyme replacement- or gene replacement therapy.

In Fabry disease, an X-linked disorder characterized by vascular complications as a result of deficient activity of alpha-galactosidase A, antibody formation towards alpha-galactosidase A has been shown to occur in a high percentage of male patients. The emergence of antibodies in the treatment of lysosomal storage disorders (LSDs) is likely to affect not only the activity of the enzymes but may also lead to altered clearance or intracellular inhibition of enzyme. Both of these effects are likely to occur in Fabry disease and the influence of these antibodies on biochemical markers as well as on storage in the skin in humans and other tissues in Fabry mice suggests that this is more than just a laboratory phenomenon. The variable nature and slowly progressive course of the disease, as well as the limited efficacy of enzyme replacement therapy, make it difficult to assess the influence on clinical outcome but it is very likely that the antibodies do have a negative effect (Hollak and Linthorst 2009).

The development of inhibitory antibodies in hemophilia is one of the most challenging aspects of current management. The incidence of antibodies in patients who have hemophilia A is estimated at 30%, whereas the incidence in hemophilia B is much lower, at approximately 3%. The antibodies, usually of the IgG4 subtype, occur early within the first 50 exposure days and are classified as low- or high-titer inhibitor according to measurement by the Bethesda unit (BU) laboratory assay (<5 BU is referred to as low titer, >5 BU as high titer) and the propensity of the antibody to anamneses after re-exposure to the antigen (Factor VIII or IX). Patients having low-titer antibodies can be treated successfully with high doses of Factor VIII or IX. Alternatively, patients having high-titer antibodies require bypassing agents, such as recombinant Factor VIIa or activated prothrombin complex concentrates, for bleeding control. Ultimately, immune tolerance induction (ITI) to eradicate the inhibitory antibodies is desired. (Rodriguez and Hoots 2008).

Thus, the method of the present invention, which involves reducing high titers of anti-therapeutic protein antibodies in diseases/conditions involving the use of, for example, ERT or gene replacement therapy with non-viral or viral vectors (or other therapeutic modality or modalities used alone or in combination which involve the administration of exogenous substances for potential therapeutic benefit, including, but not limited to DNA vaccines, siRNA, splice-site switching oligomers (SSOs) as well as RNA-based nanoparticles (RNPs) and nanovaccines (DeLong, Akhtar et al. 2009; Nandedkar 2009; Ozpolat, Sood et al. 2010)), is applicable to patients undergoing treatment for disorders including, but not limited to, the following: Pompe disease, MPS I, MPS II, MPS VI, Gaucher disease, Fabry disease, metachromatic leukodystrophy (MLD), primary immune deficiency (Shehata, Palda et al. 2010), hemophilia A and B, growth hormone deficiency, IGF-1 deficiency, and/or conditions or disease states requiring the exogenous replacement of insulin. Additional situations (i.e., conditions or disease states) where the method of the present invention could apply include, but are not limited to, treatment with substances comprising the following categories: hormones (e.g., (Fineberg, Galloway et al. 1983; Rougeot, Marchand et al. 1991)), enzymes (e.g., (Bray, Gomperts et al. 1994; Fuchs, Borowitz et al. 1994)), cytokines (e.g., (Miller, Korn et al. 1999)), growth factors (e.g., (Wadhwa, Bird et al. 1996)), antibodies (e.g., (Chatenoud, Baudrihaye et al. 1986)), receptors and antagonists (e.g., (1999)), and interferons (e.g., (Bonetti, Diodati et al. 1994; Gneiss, Koudouovoh-Tripp et al. 2009)). The term "high titers" may vary from one disease to another, and may not be necessarily be ascribed a specific numerical value. As Porter states, when an immune response to administered human proteins does occur, it appears to be largely in the form of IgG antibodies. An assessment of neutralizing activity has been the best predictor of the impact of elicited antibodies on pharmacokinetics or efficacy, but there is no model or method that can substitute at this time for direct clinical assessment" (Porter 2001).

Considerations pertaining to antibody titers can be found in the language of a Jul. 15, 1999 meeting transcript entitled "Immune Reactions Against Therapeutic and Diagnostic Biological Products" wherein the FDA Biological Response Modifiers Advisory Committee stated, "the most important criterion for assessing the significance of antibodies against therapeutic proteins is the correlation of antibody incidence and amount with clinical pharmacokinetics, pharmacodynamics, efficacy, and safety" (Reference: Center for Biologics Evaluation and Review (URL: fda[dot]gov[slash] ohrms [slash]dockets[slash]ac[slash]cber99). Qualitatively, "high titers" can thus be described as an antibody titer at which (or above which) a given patient or subject would generally experience clinical decline. It should be noted that "high antibody titers" do not necessarily develop in 100% of patients receiving ERT, for instance, but for any given disease or condition, there may be a subset of patients who have or could potentially develop high titers. Furthermore, the clinical consequences of sustained high titers may be variable between diseases and, further, between individuals with a particular disease or condition. Assays performed to detect antibodies (neutralizing or non neutralizing) sometimes have limitations which may result in non-detection or under estimation of antibody titers. In this situation, even if the titers are undetectable or at the low level, it can still result in decreased efficacy of the therapeutic agent (proteinaceous agent and/or gene therapy).

As mentioned above, patients commencing PRT and who are or may be at risk of developing an immune response to the therapeutic protein are also suitable subjects for treatment, in accordance with the method of the present invention.

In all treatment situations described above (e.g., protein replacement, gene therapy, etc.) the proteasome inhibitors described herein or elsewhere can be used in connection with additional immunomodulating therapeutic agents, or their derivatives, in various combinations and proportions thereof. This is possible even though such drugs or their derivatives are not known or described to exert their primary therapeutic effect at the level of plasma cells, the ultimate source of antibodies. Such drugs or derivatives thereof may include but are not necessarily limited to the following: rituximab (Anti CD20 monoclonal antibody), belimumab, anti CD3 antibodies, anti CD19 antibody, and anti CD22 antibody, corticosteroids (e.g. Prednisolone), rapamycin, methotrexate, WIG, cyclosphosphamide, cyclosporine A, azathioprine, mycophenolate mofetil. These additional immunomodulating agents or their derivatives include agents targeting/altering antigen presentation and/or humoral or cell mediated immune response. A preferred protocol involves the use of bortezomib together with methotrexate, rituximab and IVIG (see also FIGS. 6A and 6B):

It will be appreciated from a reading of this disclosure that while the present methods are applicable to antibodies specific for therapeutic agents (e.g., proteinaceous therapeutic agents), the methods (e.g., methods of reducing antibody titers and methods of preventing the production of antibodies) are also applicable to antibodies specific for other components of pharmaceutical compositions, including delivery vehicles (e.g., carriers, diluents excipients).

Certain aspects of the invention can be described in greater detail in the non-limiting Examples that follows.

Example 1

Suppression of Antibodies Against rhGAA by Bortezomib (Velcade®) in GAA-KO Pompe Disease Mouse Model The study described below was undertaken to evaluate the effect of bortezomib (Velcade®)—a proteasome inhibitor on the suppression of antibodies against rhGAA in a GAA-KO mouse model treated with enzyme replacement therapy (ERT) using Myozyme (alglucosidase alfa, rhGAA).

Experimental Details

GAA Knockout mice (GAA-KO)
  Six GAA-KO mice in each group (Raben, Nagaraju et al. 1998) who were all 6-8 months age.
rhGAA Administration:
  ERT was modeled in GAA-KO mice by retro-orbital injection of rhGAA (5 mg/ml [supplied by Genzyme]) over ~15 s at 20 mg/kg. When second-dose of rhGAA (20 mg/kg) was administered, pretreatment with diphenhydramine (15-25 mg/kg) by intraperitoneal injection preceded rhGAA administration by 15 min.
ELISA:
  ELISA detection of plasma anti-hGAA. An ELISA was performed as described (Ding, Hu et al. 2002). Briefly, recombinant hGAA (5 µg) in carbonate buffer was coated onto each well of a 96-well plate (Costar 3596) at 4 degree Celcius overnight. After a wash with PBS containing 0.05% Tween 20, serial dilutions of plasma samples were added in duplicate to rhGAA-coated plates and incubated at room temperature. The wells were washed with 0.05% Tween 20+PBS, incubated with a 1:2500 dilution of alkaline phosphatase-conjugated sheep anti-mouse IgG1 at room temperature for 1 h, and washed, and alkaline phosphatase substrate (p-nitrophenyl phosphate) was added. The absorbance at 411 nm was measured with a Tecan SpectraFluor (MTX Lab Systems, Vienna, Virginia, USA) microplate reader. All samples yielded absorbance values that were within the linear range of the assay at their respective dilutions.
Bortezomib:
  Bortezomib (Velcade, Millennium Pharmaceuticals) was purchased as vial containing 3.5 mg of bortezomib as sterile lyophilized powder. Proper aseptic technique was used to reconstitute it with 3.5 mL of 0.9% Sodium Chloride resulting in a final concentration of 1 mg/mL of bortezomib. It was further reconstituted with 0.9% sodium chloride at the time of administration to deliver a dose of 0.75 mg/kg/dose per mouse.
Treatment of Mice:
Bortezomib Treated Group:
  Anti-rhGAA antibodies were provoked by two doses of rhGAA administered 6 weeks apart. ELISA was performed at 3 and 6 weeks after the first rhGAA dose and 4 weeks after the second dose of rhGAA. Bortezomib was administered retroorbitally at dose of 0.75 mg/kg animal weight and was initiated 4 weeks after the second dose of rhGAA. Bortezomib administration continued for 6 total weeks with dosing occurring twice weekly and with no less than 48 hours between two successive doses. ELISA was performed at weeks 2, 4 and 6 into bortezomib administration.

Control Group:
  rhGAA administration and ELISA testing was done in the same way as described for treatment group.

Vector Treated Group:
  rhGAA administration and ELISA testing was done in the same way as described for the treatment group. 4 weeks after $2^{nd}$ rhGAA administration, AAV 2/8 (ALGAE) vector was given to each mice.

Results:

Bortezomib Treated Group:
  Antibody titers at different timepoint and treatment schedule are shown in FIG. 3A to 3F. Antibody titers appeared in 4/6 GAA-KO mice at 3 weeks (Day 21) and 6/6 GAA-KO mice at 6 weeks (Day 42) after first dose of rhGAA. In relative terms, these titer values were not high (0-1:6400). Four weeks after the second dose of rhGAA (day 91), however, the observed titers were significantly high [1:12,800 (n=5) to 1:51,200 (n=1)]. Following four doses of bortezomib (Day 105), there was a significant decline in antibody titers (1:800-1:25,600). Following 8 and 12 doses (Day 119 and Day 113) of twice weekly bortezomib treatment, a further decline in antibody titers was noted (1:200-1:6,400). ELISA data corresponding to four weeks after the $12^{th}$ dose (Day 161) of bortezomib showed titer values of 0 for 2/6 mice, and 1:200, 1:400, 1:800 and 1:6400 for the remaining 4 mice, respectively.

Control Group:
  Antibody titers appeared in GAA-KO mouse in 3 weeks and 6 weeks after first dose of rhGAA. In relative terms, these titer values were not high. Four weeks after the second dose of rhGAA, however, the observed titers were significantly high. Titers remained at high level during the follow-up period and never showed a significant decline.

Vector Treated Group:
  Antibody titers appeared in GAA-KO mouse in 3 weeks and 6 weeks after first dose of rhGAA. In relative terms, these titer values were not high. Four weeks after the second dose of rhGAA, however, the observed titers were significantly high. 4 weeks after the vector treatment antibody titers remained at high level during the follow-up period and never showed a significant decline. Further treatment with bortezomib is planned in this group to lower the antibody titers and observe the effect of vector treatment.

Endpoint Efficacy
Levels of Antibody Titers
Conclusions:
  ELISA results demonstrate that there is significant reduction of anti-rhGAA antibody titers as soon as after four doses of the proteasome inhibitor bortezomib. Further doses of bortezomib resulted in an even greater reduction of the titers and remained low. Thus, bortezomib is a highly efficacious agent in reducing antibodies to an exogenously administered therapeutic protein in the setting of an already established immune response. Other proteasome inhibitors. as well other agents acting on plasma cell in a similar or a different mechanism (e.g. MLN4924), including but not limited to those mentioned above, may show similar results given their shared mechanism of action. Similar results may also be seen if proteasome inhibitors such as bortezomib are used to lower the antibody titers against the viral or non-viral vector used for gene-therapy in various disease. This experiment serves as a model to eliminate the antibody titers against therapeutic protein replacement therapy and/or gene replacement therapy.

Example 2

Presented below is the case of an infantile Pompe disease (IPD) patient treated with ERT who, following initial clinical improvement, subsequently declined following the development of high sustained antibody titers (HSAT). An attempt at immunosuppression using non-plasma cell directed therapies (i.e., cyclophosphamide and rituximab) failed to abrogate HSAT, despite elimination of circulating mature B cells, resulting in continued clinical decline. Following failure to reduce HSAT, treatment with bortezomib alone produced a dramatic and rapid decrease in antibody titer and a concomitant improvement in clinical status. Bortezomib was then combined with rituximab (anti-CD20 monoclonal antibody; mAb), methotrexate and intravenous immunoglobulin (IVIG) to sustain reduction in titer and to attempt tolerance induction. This is the first reported use of bortezomib in the setting of HSAT to a therapeutic protein. The ability to reverse HSAT and potentially induce immune tolerance with this combination of agents represents a breakthrough in clinical use of therapeutic proteins where HSAT presents a significant obstacle to clinical benefit.

The patient, a 3.3 year old Caucasian male, was diagnosed with IPD at age 5 months. Cross-reactive immunologic material (CRIM) positive status was determined by the following criteria: Western blot testing on skin fibroblasts using monoclonal or polyclonal antibodies generated against GAA that recognize both native and recombinant forms of GAA (Kishnani et al, Pediatr. 149(1):89-97 (2006), Klinge et al, Neuromuscul. Disord. 15(1):24-31 (2005)); and a mutation analysis that revealed a missense mutation on one allele (c.307T>G) and a deletion mutation on the second (c.2481+102_2646+31 del). Disease-associated signs and symptoms were first noted at age 3 months and included hypotonia, as well as sucking and feeding difficulties. An echocardiogram at age 5 months revealed a left ventricular mass index (LVMI) of 278.6 g/m$^2$ [upper limit of normal LVMI—65 g/m$^2$ (>2 SD higher than upper limit of the age appropriate normal mean)] (Vogel et al, Pediatr. Cardiol. 12(3):143-149 (1991)). At age 6 months, the patient was started on ERT with alglucosidase alfa at 20 mg/kg every other week. Clinical improvement was observed soon after the initiation of ERT and included achievement of such motor milestones as the ability to sit unsupported, roll over, raise arms against gravity and bear weight on his lower extremities. At week 38 of ERT (age 15 months) LVMI decreased from his baseline/pre-ERT value of 278.6 g/m$^2$ to 135 g/m$^2$.

Figure 4:
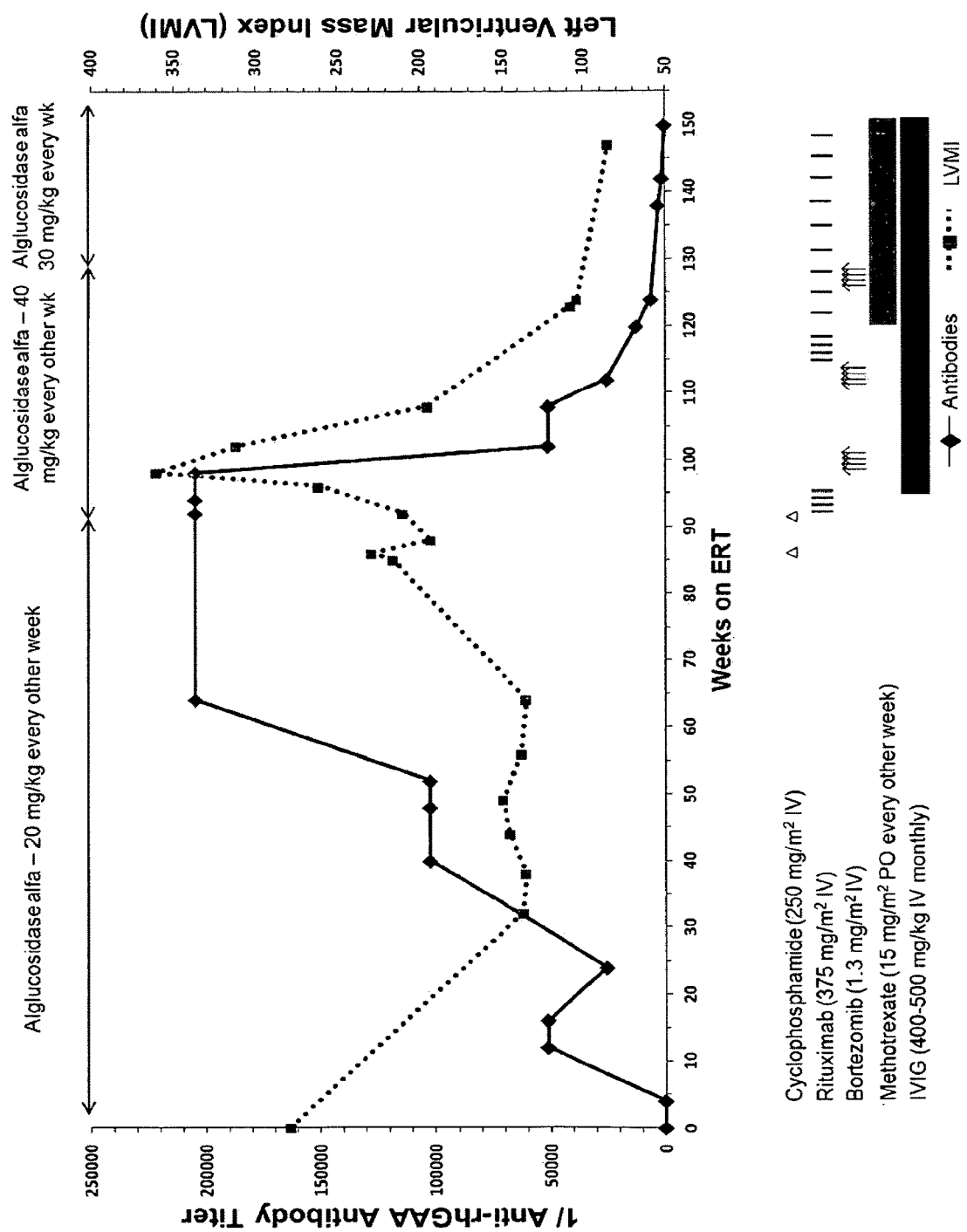
FIG. 4. Following unsuccessful immunomodulation with cyclophosphamide (250 mg/m$^2$) and rituximab (375 mg/m$^2$; weeks 86 to 95), bortezomib (Velcade®) was administered intravenously (IV) twice weekly at 1.3 mg/m$^2$ of body surface area according to a standard dosing regimen (days 1, 4, 8 and 11; equivalent to one cycle of bortezomib) (Velcade. [Package Insert]. Pamphlet. Cambridge (Mass.): Millenium Pharmaceuticals, Inc. (2010) during weeks 99 and 100 (cycle 1), weeks 110 and 111 (cycle 2) and weeks 127 and 128 (cycle 3) of ERT. Monthly intravenous immunoglobulin (IVIG) was administered at the start of the first cycle of bortezomib to passively maintain immunity and to potentially contribute to immunomodulation. Following a second cycle of bortezomib with continued ERT, a total of four weekly doses of rituximab at 375 mg/m$^2$ was administered in addition to biweekly methotrexate at 15 mg/m$^2$ PO. Rituximab was thereafter administered on a monthly basis. Anti-rhGAA IgG antibody titers and left ventricular mass index (LVMI; g/m$^2$; secondary y-axis) over time are shown above by a solid black line and a dashed red line, respectively (the upper limit of normal LVMI is 65 g/m$^2$) (Vogel et al, Pediatr. Cardiol. 12(3):143-149 (1991)).

Rising Antibody Titers and Subsequent Clinical Decline
  This patient was serially evaluated for anti-rhGAA IgG antibodies by Genzyme Corp. MA, as recommended in the Myozyme® package insert (Velcade. [Package Insert]. Pamphlet. Cambridge (Mass.): Millenium Pharmaceuticals, Inc. (2010)). From a seronegative status at week 4 of ERT, anti-rhGAA antibody titers (antibody titers) rose to 1:51,200 at 16 weeks on ERT, 1:102,400 at weeks 40, 48 and 52 and peaked at 1:204,800 at week 64 of ERT. Titers were maintained at 1:204,800 through week 86. Concomitant with rising antibody titers was a progressive decline in clinical status, including loss of previously acquired developmental milestones and worsening cardiomyopathy. By age 19 months (55 weeks post-ERT initiation) the patient became full-time invasive ventilator dependent and tube feeds were required. Concomitantly, LVMI increased from 135 g/m² at week 38 to 228.6 g/m² at week 86. Anti-rhGAA IgG antibody titers and LVMI values over time are shown in FIG. 4.

Immunomodulation Attempts with Cyclophosphamide and Rituximab

Due to HSAT and concurrent clinical decline, immune tolerance induction (ITI) was attempted: cyclophosphamide (250 mg/m²) monotherapy was administered at weeks 86 and 92 of ERT, followed by rituximab (375 mg/m²) from weeks 92 to week 95 post-ERT initiation (FIG. 4), based on published reports (Hunley et al, Pediatrics 114(4):e532-e535 (2004), Mendelsohn et al, N. Engl. J. Med. 360(2):194-195 (2009)). Despite elimination of B cells from peripheral blood, as evidenced by a CD19 count of 0% at week 95, antibody titers remained persistently high, sustained, and unchanged at 1:204,800 at week 98 and the patient continued to decline clinically. LVMI was 261 g/m² at week 96 of ERT and peaked at 360 g/m² at week 98 of ERT (age 28.5 months). Increasing LVMI deterioration resulted in an almost-complete left ventricular cavitary obstruction in addition to significant left ventricular outflow tract obstruction (LVOTO; peak velocity 5.3 m/s). The patient was unable to move his arms or legs and his voluntary motor activity was limited to eye movements.

Immunomodulation Using Bortezomib and Subsequent Clinical Improvement

Given the dire prognosis of this child and reasoning that rituximab-resistant, antibody-secreting plasma cells had to be eliminated, and after discussion with the Northern California Regional Kaiser Genetic Diseases Treatment Advisory Board and obtaining written parental informed consent, a trial of bortezomib was commenced with the hope that it would eliminate a sufficient number of the long-lived antibody-secreting plasma cells and decrease the antibody titer quickly. Details of the immunomodulatory strategy using bortezomib are described in FIG. 4.

Figure 5:
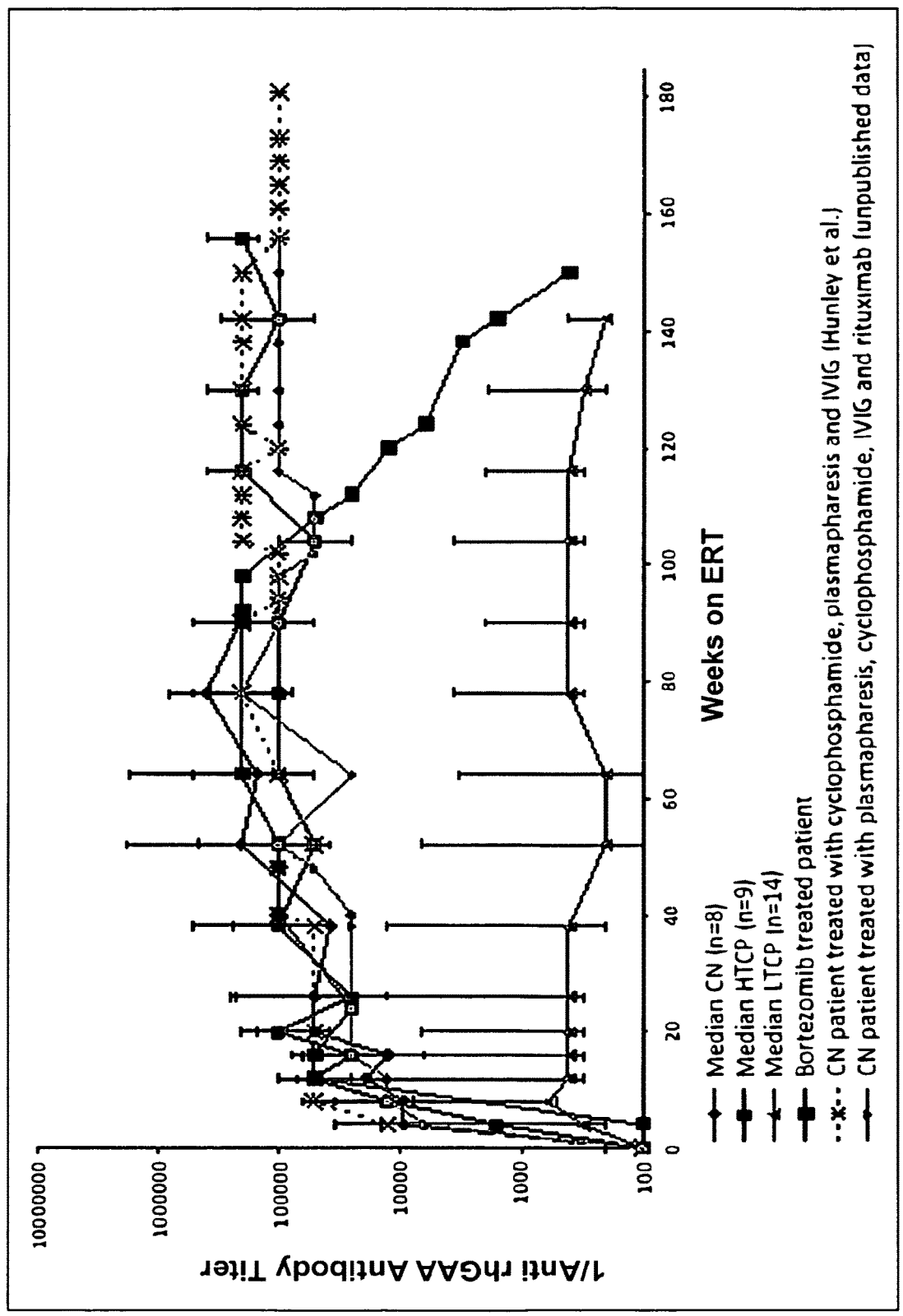
FIG. 5. Comparison of anti-rhGAA antibody titers seen in the patient (blue) presented here versus antibody titers seen in CRIM negative (CN; black), high titer CRIM positive (HTCP; red), low titer CRIM positive (LTCP; green) and 2 CN patients treated with non-bortezomib-based immunomodulatory regimens (purple and cyan). The CN, HTCP and LTCP patients were treated with ERT alone. High sustained antibody titers (≥1:51,200) beyond week 26 resulted in poor clinical outcome in the CN and HTCP groups as compared to the LTCP group who have significantly lower antibody titers and better clinical outcomes to ERT (Banugaria et al. 2011). Commencement of immunomodulatory therapy with bortezomib at week 99 in the patient described was associated with a significant decline in antibody titers. Titers are now within a similar range to the LTCP group. This is in contrast to 2 CN patients with high sustained antibody titers (HSAT), treated with different immunomodulatory regimens. One CN patient (purple) was treated from week 26 to 46 of ERT with frequent cyclophosphamide, plasmapheresis and intravenous immunoglobulin G and had persistence of HSAT (1:102,400) through week 181 as reported by Hunley et al (Pediatrics 114(4):e532-e535 (2004)). Similarly, a second CN patient (cyan) treated with plasmapheresis, cyclophosphamide, IVIG and rituximab from week 17 to 103 of ERT had persistence of HSAT (1:102,400) through week 156 of ERT (unpublished data).

Following the first cycle of bortezomib (i.e., weeks 99 through 100) as monotherapy, antibody titers decreased from 1:204,800 to 1:51,200 at week 102 of ERT. Cycle two of bortezomib (i.e., weeks 110 through 111) was combined with rituximab, methotrexate and IVIG to preclude activation of rhGAA specific naïve and memory B and T cells and facilitate tolerance induction. This treatment resulted in a further decline of the antibody titer: 1:12,800 at week 120 and 1:6,400 at week 124. Following a third round of bortezomib in combination with rituximab and methotrexate, antibody titers were 1:400 at week 150 of ERT. The decline in anti-rhGAA antibody titers in this bortezomib treated patient over time is in stark contrast to the persistence of HSAT in CRIM negative and high-titer CRIM positive patients, as well as in patients treated with a non-bortezomib-based immunomodulatory regimen (Hunley et al, Pediatrics 114(4):e532-e535 (2004)). (FIG. 5)

The observed reduction in antibody titers, from 1:204,800 to 1:400, following implementation of an immunomodulation strategy using bortezomib was in close temporal association with marked clinical improvement: from a pre-immunomodulation (i.e., pre-bortezomib) status of complete flaccid paralysis and fulminant cardiac failure, to a rapid and relatively marked improvement in clinical outcome measures for cardiac function (e.g., LVMI and LVOTO), pulmonary function (i.e., time spent on invasive ventilation) and a remarkable reacquisition of previously lost motor milestones together with an increasingly greater capacity to execute voluntary motor movements (e.g., limb movements, speech). LVMI (FIG. 4) dropped from 360 g/m² at week 98 to 195 g/m² at week 108, to 104 g/m² at week 124 and 85 g/m² at week 147 of ERT following first, second and third round of bortezomib, respectively with significant reduction of LVOTO (peak velocity 3.2 m/s). Further motor gains were observed as demonstrated by a regained ability to move his fingers and toes, bend his knees and nod his head in addition to recovery of muscles of facial expression. The treatment regimen was well tolerated with no apparent side effects noted.

At present, there are over 75 therapeutic proteins approved by the Food and Drug Administration (FDA) for life-threatening and debilitating chronic diseases with many more under development. A principal problem precluding the full clinical benefit otherwise derived from the use of these agents for their intended purposes relates to elicitation of immune responses arising from exposure to a therapeutic protein that is immunologically perceived as being non-self (i.e., foreign) antigen. This represents a unifying theme and important consideration for patients actually or potentially treated for a number of protein deficiency disorders which have historically included, but are not limited to, Pompe disease, mucopolysaccharidosis types I, II, and VI, Fabry disease and hemophilias A and B (Ragni et al, Haemophilia 15(5):1074-1082 (2009), Hollak and Linthorst, Mol. Genet. Metab. 96(1):1-3 (2009), Wang et al, Nat. Biotechnol. 25(8):901-908 (2008)). Indeed, the prognosis of patients who develop HSAT against ERT is poor, and can be fatal (Ragni et al, Haemophilia 15(5):1074-1082 (2009), Kishnani et al, Mol. Genet. Metab. 99(1):26-33 (2010), Banugaria et al, Genet. Med. (In Press)). In addition to the human toll, hundreds of millions of dollars are wasted in the use of therapeutic proteins in patients who are not responding to the treatment because of antibodies developed against them (Kishnani et al, Mol. Genet. Metab. 99(1):26-33 (2010), Wang et al, Nat. Biotechnol. 25(8):901-908 (2008), Hartung et al, Eur. J. Neurol. 12(8):588-601 (2005)). Therefore, investigation of novel immunomodulatory strategies to preclude or reverse immune responses and to induce immune tolerance in this setting is critical not only for improving the functional status of individual patients but also for minimizing wasteful financial expenditures.

The negative impact of HSAT in patients with IPD, both CRIM negative and a subset of CRIM-positive patients who generate such high titer responses and show clinical decline, has been demonstrated previously. Interestingly, the antibody responses of the latter patients lack documented neutralizing activity, either of enzyme catalysis or cellular uptake Kishnani et al, Mol. Genet. Metab. 99(1):26-33 (2010), Banugaria et al, Genet. Med. (In Press)), as was the case in this patient. However, high titer antibody responses to protein therapeutics have been shown to mistarget the administered protein to FcR bearing cells and to cause aberrant trafficking within cells accounting for the loss of efficacy (Brooks, Mol. Genet. Metab. 68(2):268-275 (1999)).

Described above is the first successful use of bortezomib as an immunomodulatory agent in the setting of a well-established immune response to a therapeutic protein. In this case report of an IPD patient, treatment initiation with bortezomib was rapidly followed by sustained reductions in HSAT. The rapid, marked reduction in antibody titers (1:204,800 to 1:51,200) occurred within 3 weeks of start of bortezomib. There has been a further reduction over the next 41 weeks, with the most recent antibody titer at 1:400. This represents a 512-fold [nine-log (base 2)] decline in titers vs. initial titers of 1:204,800. Notably, and most importantly, the marked and sustained decrease in antibody titers was associated with significant, durable improvement across all clinical outcome measures and the patient continues to improve.

This is the first known reported case where there has been successful induction of a prolonged decline in HSAT in Pompe disease. This case clearly and dramatically demonstrates the direct relationship of the antibody response (titers and duration) and clinical response. Although the mechanism of action of bortezomib is not precisely known in this case, it appears to be principally due to proteasome inhibition in both short-lived and long-lived plasma cells—the direct sources of antibody production and theoretical basis for its initial use in the clinical context described here. However, as a proteasome inhibitor, bortezomib may have an additional mode of action directly on muscle in the context of IPD. The ubiquitin-proteasome system (UPS) is believed to degrade the major contractile skeletal muscle proteins and to play a critical role in muscle wasting. Muscle wasting is a prominent feature of IPD similar to other muscle wasting disease states such as cancer cachexia, sepsis, diabetes and metabolic acidosis, in which expression of the ubiquitin-proteasome proteolytic pathway is increased in skeletal muscle (Hirschhorn and Reuser, Glycogen Storage Disease Type II: Acid a-Glucosidase (Acid Maltase) Deficiency [Internet Resource; Computer File Date of Entry: 20090331], New York: McGraw-Hill (2009), Available from: Lecker et al, J. Nutr. 129(IS Suppl):2275-237S (1999), Tisdale, Curr. Opin. Support Palliat Care 1(4):287-292 (2007); Hirschhorn et al, Glycogen Storage Disease Type II: Acid a-Glucosidase (Acid Maltase) Deficiency [Internet Resource; Computer File Date of Entry: 20090331]. New York: McGraw-Hill; 2009. Available from: URL: genetics [dot]accessmedicine[dot]com/). Thus, blockade of the proteasome in muscle has the potential to mitigate skeletal muscle wasting and damage. Such has been demonstrated preclinically in Duchenne and Becker muscular dystrophies as well as in rat models of denervation-induced muscular atrophy (Gazzerro et al, Am. J. Pathol. 176(4):1863-1877 (2010), Beehler et al, Exp. Biol. Med. (Maywood) 231(3): 335-341 (2006)).

A combination of drugs which target B cells, helper T cells, and plasma cells, as used in this patient, is needed to achieve long term remission of antibodies and potential induction of immune tolerance, as depicted in FIG. 1. Such a combination precludes generation of new plasma cells and may prevent secretion of anti-apoptotic and stimulatory cytokines from T cells. In this case scenario, the combination of rituximab, methotrexate and IVIG in addition to bortezomib appeared both safe and efficacious, each drug acting on a different part of the pathway leading to antibody production (FIG. 1). Given the dramatic suppression of immunity, the patient was supplemented with monthly IVIG for infection prophylaxis and to potentially contribute to immunomodulation (Hall, Pharmacotherapy 13(6):564-573 (1993)).

The immunomodulatory approach described here can be used to improve outcomes in patients affected by entrenched immune responses to replacement therapies for underlying primary disease (as occurs in lysosomal storage diseases, severe hemophilia A and B, and other conditions) whereby the therapeutic protein elicits a robust antibody-mediated immune response that reduces overall efficacy of the therapeutic protein. It may also prove successful in addressing autoimmune disorders which fail to respond to agents targeting T and B cells such as rituximab and methotrexate. Thus, this immunomodulatory approach should be considered in a variety of settings in which the immune response is implicated in disease pathogenesis or in abrogating effectiveness of protein therapeutics.

Example 3

Patient is 5.6 year old Caucasian male diagnosed with Pompe disease at the age of 3.5 years based on reduced GAA activity in muscle and confirmed by mutation analysis (homozygous for c.1655T>C). Cross reactive immunologic material (CRIM) testing through western blot on skin fibroblas revealed CRIM positive status. Patient initially presented with respiratory failure and required BiPAP. After a brief unsuccessful trial of BiPAP the decision was made to perform tracheostomy with ventilation support at 3.5 years. ERT with alglucosidase alfa was commenced at the age of 3.6 years. Anti rhGAA antibody titers continued to rise and following 90 weeks of ERT the titers were 1:204,800. Along with the rise in antibody titers this patient showed clinical deterioration. Given the rise in antibody titers and concurrent clinical decline, bortezomib based immunomodulating regimen (described above in Example 2) was initiated. Following three rounds of bortezomib in combination with monthly rituximab and IVIG and biweekly methotrexate, the titers have now declined from 1:204,800 (week 90) to 1:12,800 (at week 129) with significant clinical improvement. There is a significant reduction in ventilation requirement along with increase in overall strength and patient has started weaning off vent. There is marked improvement of motor function, speech and swallowing at the most recent assessment (5.6 years). The treatment regimen was well tolerated with no apparent side effects noted.

Example 4

Patient is a 3.8 year-old Caucasian male diagnosed with Pompe disease at the age of 3.5 months based on the reduced activity of GAA and confirmed by mutation analysis (c.1654delC, c.2560C>T). Cross-reactive immunologic material (CRIM) testing showed a CRIM-negative status on skin fibroblasts. Age at ERT start was 4.5 months. Patient was seronegative at baseline for anti-rhGAA antibody titers. Titers continued to rise to a maximum of 819,200 at Week 86 of ERT. Despite treatment with rituximab and methotrexate, the titers stayed in the range of 409,600 to 819,200 from week 86 to Week 151 of ERT. Concurrent with the rise in antibody titers, there was marked clinical deterioration. Patient was started on a bortezomib-based immunomodulatory regimen described in Example 2. Following two rounds of bortezomib, in combination with rituximab, methotrexate and IVIG, there was a decline in titers from 409,600 at Week 151 to 51,200 at Week 179 of ERT. This decline in titers was associated with significant clinical improvement with no apparent side effects.

Example 5

Patient is a 1.2 year-old Asian-Indian male diagnosed with infantile Pompe disease at the age of 2.0 months based on the reduced activity of GAA and confirmed by mutation analysis. Cross-reactive immunologic material (CRIM) testing showed a CRIM-negative status. Age at ERT start was 2.7 months. Patient was seronegative at baseline for anti-rhGAA antibody titers. Titers continued to rise to a maximum of 51,200 at Week 13 of ERT. Based on clinical experience and poor outcomes in CRIM-negative patients despite ERT, this patient was started on a bortezomib-based immunomodulatory regimen at Week 13 of ERT. Following two rounds of bortezomib in combination with rituximab, methotrexate and IVIG, titers have now declined to 12,800 at Week 48 of ERT. Along with achievement of new motor milestones and improvement in cardiopulmonary status there were no apparent side effects.

All documents and other information sources cited herein are hereby incorporated in their entirety by reference.

REFERENCES (1999). "TNF neutralization in MS: results of a randomized, placebo-controlled multicenter study. The Lenercept Multiple Sclerosis Study Group and The University of British Columbia MS/MRI Analysis Group." *Neurology* 53(3): 457-465.

Banugaria et al, Genetics in Medicine 13(8) (2011)

Bessis, N., F. J. GarciaCozar, et al. (2004). "Immune responses to gene therapy vectors: influence on vector function and effector mechanisms." *Gene Ther* 11 Suppl 1: S10-17.

Boutin, S., V. Monteilhet, et al. (2010). "Prevalence of serum IgG and neutralizing factors against adeno-associated virus types 1, 2, 5, 6, 8 and 9 in the healthy population: implications for gene therapy using AAV vectors." *Hum Gene Ther.*

Chatenoud, L., M. F. Baudrihaye, et al. (1986). "Restriction of the human in vivo immune response against the mouse monoclonal antibody OKT3." *J Immunol* 137(3): 830-838.

Chauhan, D., L. Catley, et al. (2005). "A novel orally active proteasome inhibitor induces apoptosis in multiple myeloma cells with mechanisms distinct from Bortezomib." *Cancer Cell* 8(5): 407-419.

Demo, S. D., C. J. Kirk, et al. (2007). "Antitumor activity of PR-171, a novel irreversible inhibitor of the proteasome." *Cancer Res* 67(13): 6383-6391.

Dick, L. R. and P. E. Fleming "Building on bortezomib: second-generation proteasome inhibitors as anti-cancer therapy." *Drug Discov Today* 15(5-6): 243-249.

Dickson et al, J. Clin. Invest. 118(8):2868-2876 (2008).

Everly, M. J., J. J. Everly, et al. (2008). "Bortezomib provides effective therapy for antibody- and cell-mediated acute rejection." *Transplantation* 86(12): 1754-1761.

Franco, L. M., B. Sun, et al. (2005). "Evasion of immune responses to introduced human acid alpha-glucosidase by liver-restricted expression in glycogen storage disease type II." *Mol Ther* 12(5): 876-884.

Hawes, M. L., W. Kennedy, et al. (2007). "Differential muscular glycogen clearance after enzyme replacement therapy in a mouse model of Pompe disease." *Mol Genet Metab* 91(4): 343-351.

Hirschhorn, R. and A. J. J. Reuser (2009). Glycogen Storage Disease Type II: Acid α-Glucosidase (Acid Maltase) Deficiency. *Scriver's OMMBID the online metabolic & molecular bases of inherited disease.* D. Valle and C. R. Scriver. New York, McGraw-Hill.

Hollak, C. E. and G. E. Linthorst (2009). "Immune response to enzyme replacement therapy in Fabry disease: impact on clinical outcome?" *Mol Genet Metab* 96(1): 1-3.

Hug, G. (1978). "Pre- and postnatal pathology, enzyme treatment, and unresolved issues in five lysosomal disorders." *Pharmacol Rev* 30(4): 565-591.

Kakkis et al, Proc. Natl. Acad. Sci. USA 101(3) 829-834 (2004).

Kishnani, P. S., D. Corzo, et al. (2009). "Early treatment with alglucosidase alpha prolongs long-term survival of infants with Pompe disease." *Pediatr Res* 66(3): 329-335.

Kishnani, P. S., D. Corzo, et al. (2007). "Recombinant human acid [alpha]-glucosidase: major clinical benefits in infantile-onset Pompe disease." *Neurology* 68(2): 99-109.

Kishnani, P. S., P. C. Goldenberg, et al. (2009). "Cross-reactive immunologic material status affects treatment outcomes in Pompe disease infants." *Mol Genet Metab.*

Kishnani, P. S., W. L. Hwu, et al. (2006). "A retrospective, multinational, multicenter study on the natural history of infantile-onset Pompe disease." *J Pediatr* 148(5): 671-676.

Kishnani, P. S., M. Nicolino, et al. (2006). "Chinese hamster ovary cell-derived recombinant human acid alpha-glucosidase in infantile-onset Pompe disease." *J Pediatr* 149(1): 89-97.

Kupperman, E., E. C. Lee, et al. "Evaluation of the proteasome inhibitor MLN9708 in preclinical models of human cancer." *Cancer Res* 70(5): 1970-1980.

Lecker, S. H., V. Solomon, et al. (1999). "Muscle protein breakdown and the critical role of the ubiquitin-proteasome pathway in normal and disease states." *J Nutr* 129(1S Suppl): 227S-237S.

Manno et al, Nature Medicine 12:342-347 (2006)

Mendelsohn, N. J., Y. H. Messinger, et al. (2009). "Elimination of antibodies to recombinant enzyme in Pompe's disease." *N Engl J Med* 360(2): 194-195.

Moreau, P., V. Coiteux, et al. (2008). "Prospective comparison of subcutaneous versus intravenous administration of bortezomib in patients with multiple myeloma." *Haematologica* 93(12): 1908-1911.

Neubert, K., S. Meister, et al. (2008). "The proteasome inhibitor bortezomib depletes plasma cells and protects mice with lupus-like disease from nephritis." *Nat Med* 14(7): 748-755.

Nicolino, M., B. Byrne, et al. (2009). "Clinical outcomes after long-term treatment with alglucosidase alfa in infants and children with advanced Pompe disease." *Genet Med* 11(3): 210-219.

Phupong, V., S. Shuangshoti, et al. (2005). "Prenatal diagnosis of Pompe disease by electron microscopy." *Arch Gynecol Obstet* 271(3): 259-261.

Raben et al, J. Biol. Chem. 273(30:19086-19092 (1998).

Raben, N, S Takikita, et al. (2007). "Deconstructing Pompe disease by analyzing single muscle fibers: to see a world in a grain of sand." *Autophagy* 3(6): 546-552.

Rodriguez, N. I. and W. K. Hoots (2008). "Advances in hemophilia: experimental aspects and therapy." *Pediatr Clin North Am* 55(2): 357-376, viii.

Shehata, N., V. Palda, et al. (2010). "The use of immunoglobulin therapy for patients with primary immune deficiency: an evidence-based practice guideline." *Transfus Med Rev* 24 Suppl 1: S28-50.

Shirley, R. B., I. Kaddour-Djebbar, et al. (2005). "Combination of proteasomal inhibitors lactacystin and MG132 induced synergistic apoptosis in prostate cancer cells." *Neoplasia* 7(12): 1104-1111.

Sun, B., A. Bird, et al. (2007). "Enhanced response to enzyme replacement therapy in Pompe disease after the induction of immune tolerance." *Am J Hum Genet* 81(5): 1042-1049.

Sun et al, Mol. Ther. 18(2):353-360 (2010).

Tisdale, M. J. (2007). "Is there a common mechanism linking muscle wasting in various disease types?" *Curr Opin Support Palliat Care* 1(4): 287-292.

van den Hout, H. M., W. Hop, et al. (2003). "The natural course of infantile Pompe's disease: 20 original cases compared with 133 cases from the literature." *Pediatrics* 112(2): 332-340.

Wang, J., J. Lozier, et al. (2008). "Neutralizing antibodies to therapeutic enzymes: considerations for testing, prevention and treatment." *Nat Biotechnol* 26(8): 901-908.

Williamson, M. J., J. L. Blank, et al. (2006). "Comparison of biochemical and biological effects of ML858 (salinosporamide A) and bortezomib." *Mol Cancer Ther* 5(12): 3052-3061.

The invention claimed is:

1. A method of improving the efficacy of gene replacement therapy, the method comprising:
   administering to a treatment-naive patient having glycogen storage disease type II (GSD II) a viral vector encoding human acid glucosidase alfa (rhGAA); and
   administering to the patient a therapeutically effective amount of bortezomib,
       wherein, following the administering of the bortezomib, the titer of antibodies specific for the viral vector, the encoded rhGAA, or both is reduced, thereby improving the efficacy of the gene replacement therapy.

2. The method of claim 1, wherein the method further comprises administering to the patient a compound that targets or alters antigen presentation or humoral or cell mediated immune response.

3. The method of claim 1, wherein the method further comprises administering to the patient rituximab, methotrexate, and intravenous gamma globulin.

4. The method of claim 1, wherein the bortezomib is administered prior to or after the viral vector.

5. The method of claim 1, wherein the viral vector is selected from the group consisting of adenovirus, adeno-associated virus, lentivirus, and herpes simplex virus.

6. The method of claim 1, wherein the method further comprises administering the bortezomib two or more times.

7. The method of claim 1, wherein the administering of bortezomib comprises oral administration, intravenous administration, intramuscular administration, subcutaneous administration, intrathecal administration, or topical administration.

8. The method of claim 1, wherein following the administering steps, the patient experiences a clinical benefit.

9. A method of reducing the risk of developing high sustained antibody titers (HSAT), the method comprising:
   administering to a treatment-naive patient having glycogen storage disease type II (GSD II) gene replacement therapy comprising a viral vector encoding human acid glucosidase alfa (rhGAA); and
   administering to the patient a therapeutically effective amount of bortezomib,
       wherein, following the administering of the bortezomib, the patient's risk of developing HSAT to the viral vector, the encoded rhGAA, or both is reduced.

10. The method of claim 9, wherein the viral vector is selected from the group consisting of adenovirus, adeno-associated virus, lentivirus, and herpes simplex virus.

11. The method of claim 9, wherein the method further comprises administering to the patient a compound that targets or alters antigen presentation or humoral or cell mediated immune response.

12. The method of claim 9, wherein the method further comprises administering to said patient rituximab, methotrexate, and intravenous gamma globulin.

13. The method of claim 9, wherein the bortezomib is administered prior to or after the viral vector.

14. The method of claim 9, wherein the method further comprises administering the proteasome inhibitor two or more times.

15. The method of claim 9, wherein the administering of bortezomib comprises oral administration, intravenous administration, intramuscular administration, subcutaneous administration, intrathecal administration, or topical administration.

16. The method of claim 9, wherein following the administering steps, the patient experiences a clinical benefit.

* * * * *

UNITED STATES PATENT AND TRADEMARK OFFICE
CERTIFICATE OF CORRECTION

PATENT NO. : 12,290,549 B2  
APPLICATION NO. : 17/125885  
DATED : May 6, 2025  
INVENTOR(S) : Priya S. Kishnani et al.

Page 1 of 1

It is certified that error appears in the above-identified patent and that said Letters Patent is hereby corrected as shown below:

In the Claims

In Claim 1, Column 27, Line 13, delete "(rhGAA)" and insert -- (hGAA) --.

In Claim 1, Column 27, Line 18, delete "rhGAA" and insert -- hGAA --.

In Claim 9, Column 28, Line 8, delete "(rhGAA)" and insert -- (hGAA) --.

In Claim 9, Column 28, Line 14, delete "rhGAA" and insert -- hGAA --.

In Claim 14, Column 28, Line 29, delete "the proteosome inhibitor" and insert -- the bortezomib --.

Signed and Sealed this  
Twenty-third Day of September, 2025

John A. Squires  
*Director of the United States Patent and Trademark Office*